(12) United States Patent
Gosik-Wolfe

(10) Patent No.: US 12,383,413 B2
(45) Date of Patent: Aug. 12, 2025

(54) IMPLANT EXTRACTOR

(71) Applicant: Shukla Medical, St. Petersburg, FL (US)

(72) Inventor: Adam Gosik-Wolfe, Tampa, FL (US)

(73) Assignee: Shukla Medical, St. Petersburg, FL (US)

( * ) Notice: Subject to any disclaimer, the term of this patent is extended or adjusted under 35 U.S.C. 154(b) by 352 days.

(21) Appl. No.: 17/204,385

(22) Filed: Mar. 17, 2021

(65) Prior Publication Data

US 2021/0290411 A1 Sep. 23, 2021

Related U.S. Application Data

(60) Provisional application No. 62/991,940, filed on Mar. 19, 2020.

(51) Int. Cl.
*A61F 2/46* (2006.01)
*A61B 17/92* (2006.01)

(52) U.S. Cl.
CPC ............ *A61F 2/4612* (2013.01); *A61B 17/92* (2013.01); *A61F 2002/4619* (2013.01); *A61F 2002/4628* (2013.01)

(58) Field of Classification Search
CPC ............. A61B 17/92; A61F 2002/4619; A61F 2002/462; A61F 2002/4622; A61F 2002/4625; A61F 2002/4627; A61F 2002/4628; A61F 2/4603; A61F 2/46; A61F 2/4605–4612; B25B 13/52; B25B 7/12
See application file for complete search history.

(56) References Cited

U.S. PATENT DOCUMENTS

| | | | | |
|---|---|---|---|---|
| 244,269 | A | * | 7/1881 | Lovrien .................... B25B 7/10 81/402 |
| 1,348,832 | A | * | 8/1920 | Magnan .................... B25B 7/04 81/437 |
| 2,942,508 | A | * | 6/1960 | Bannister .................. B25B 7/14 81/352 |
| 6,041,680 | A | * | 3/2000 | Wang ...................... B25B 7/123 81/409 |
| 2006/0200162 | A1 | | 9/2006 | Farling et al. |
| 2007/0163084 | A1 | * | 7/2007 | Liou ........................ B25G 3/18 16/436 |
| 2015/0246432 | A1 | | 9/2015 | William et al. |
| 2016/0221132 | A1 | * | 8/2016 | Wong ........................ B25B 7/12 |
| 2016/0270929 | A1 | * | 9/2016 | Sweitzer ................. A61F 2/461 |
| 2017/0189204 | A1 | * | 7/2017 | Riemhofer ......... A61B 17/8877 |
| 2019/0076994 | A1 | * | 3/2019 | Blumenthal ............. B25B 7/02 |
| 2019/0216454 | A1 | | 7/2019 | Daniel et al. |

OTHER PUBLICATIONS

Extended European Search Results for EP 21382229.9, dated Jul. 5, 2021.

* cited by examiner

*Primary Examiner* — Amy R Sipp
(74) *Attorney, Agent, or Firm* — Kim IP Law Group LLC

(57) ABSTRACT

An implant extractor including a second arm having a proximal end and a distal end, and a first arm having a proximal end for attachment to an extraction device. The first arm additionally has a distal end for attachment to a first jaw, and an adjustment mechanism including an adjuster and a lever. The lever has a proximal end engaged with the adjuster and a distal end pivotably connected to the second arm. The implant extractor additionally includes a link pivotably connected to the first and second arms, the link having a distal end for attachment to a second jaw.

19 Claims, 30 Drawing Sheets

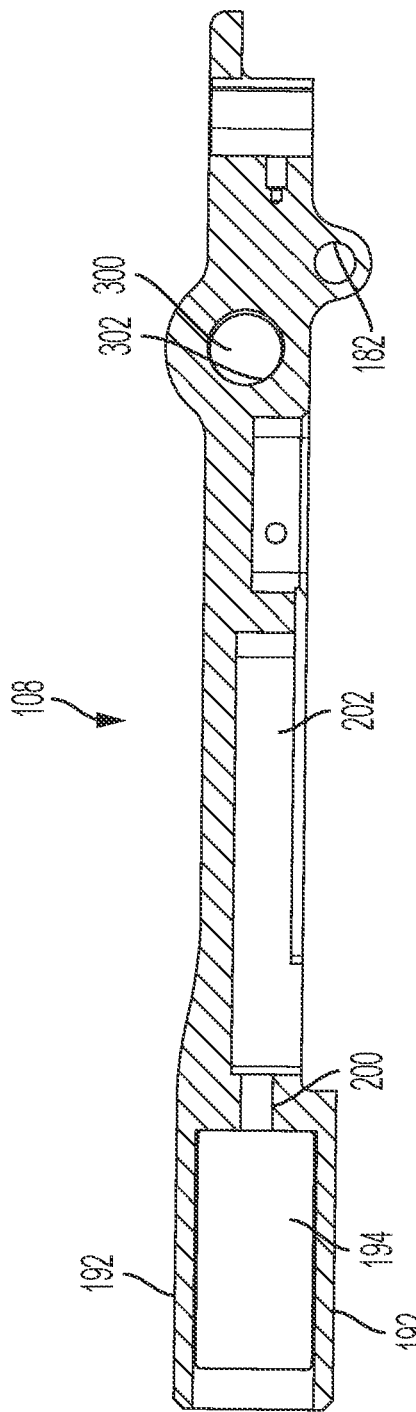
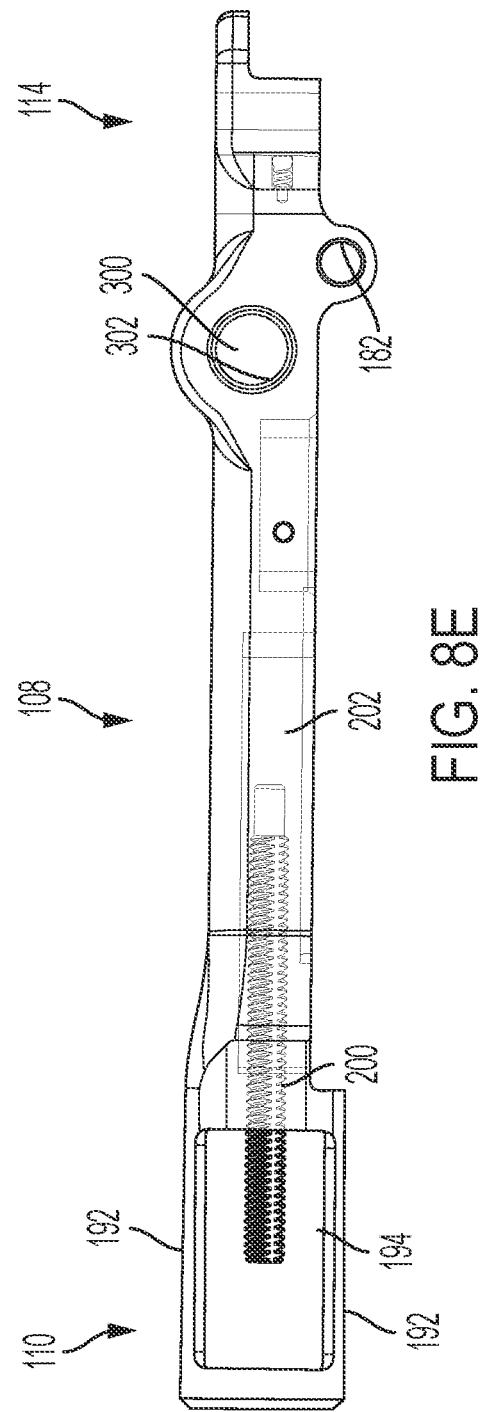

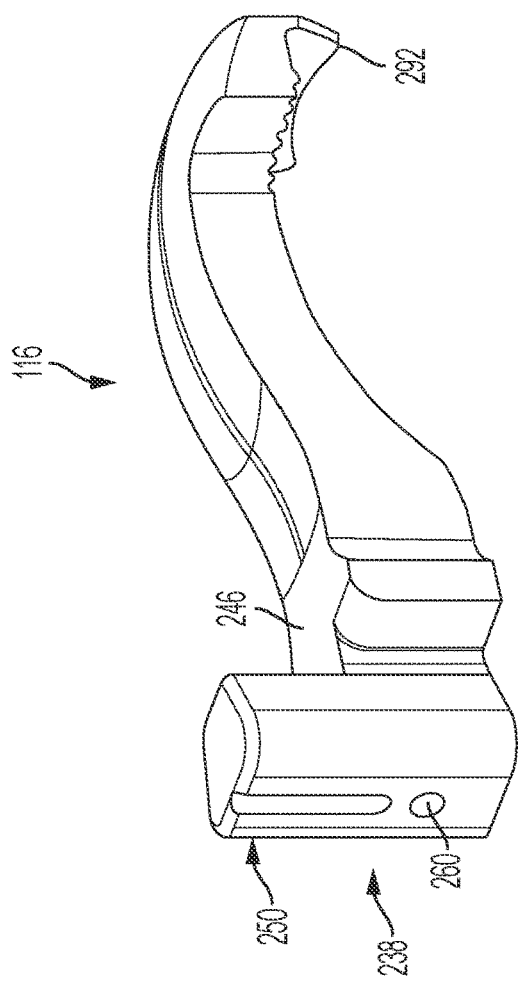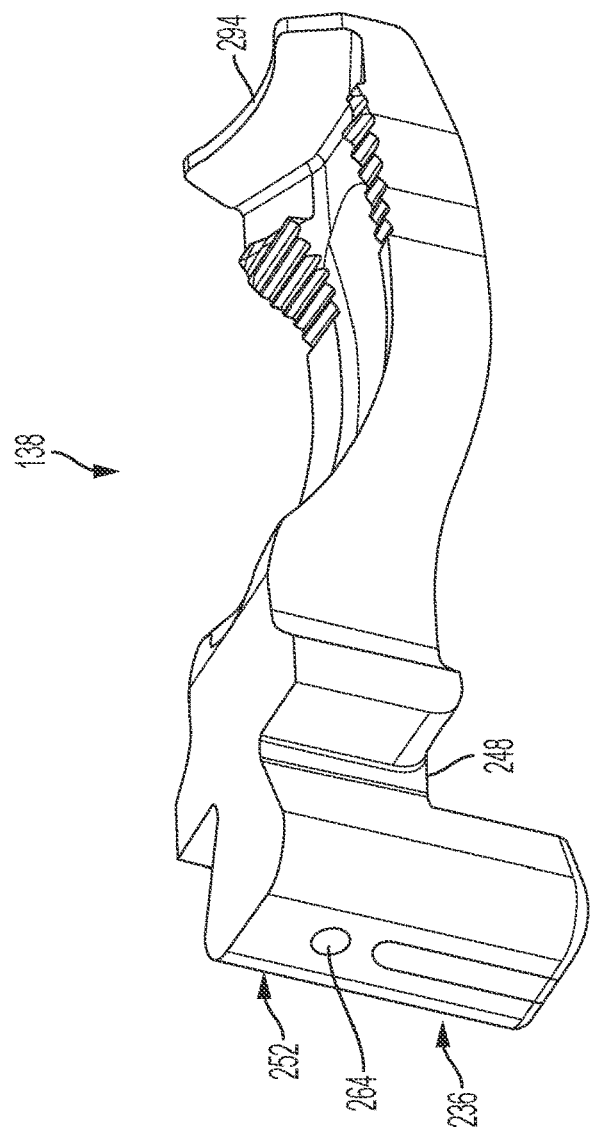

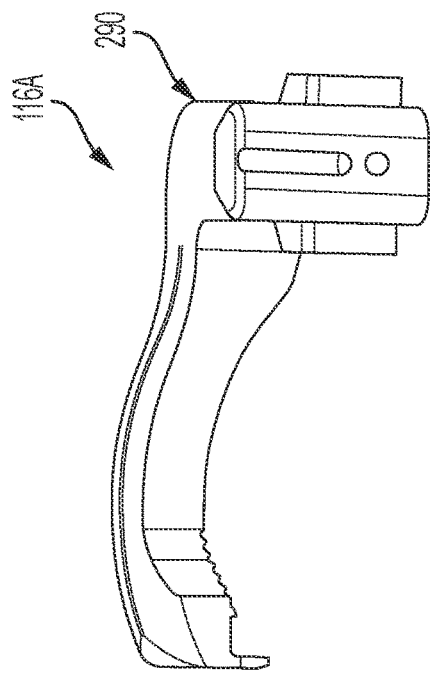
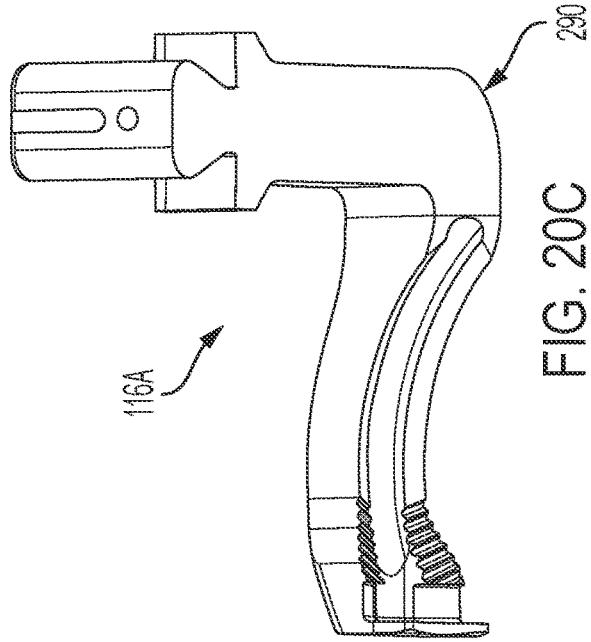
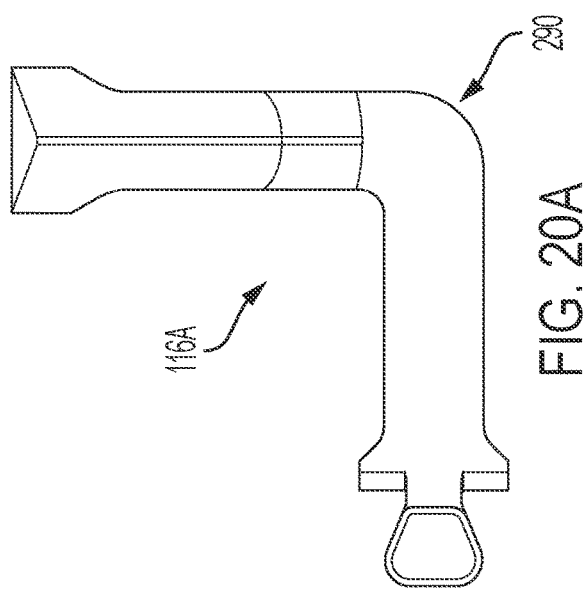
FIG. 20A
FIG. 20B
FIG. 20C

IMPLANT EXTRACTOR

CROSS-REFERENCE TO RELATED APPLICATION

This application claims the benefit under 35 U.S.C. § 119(e) to U.S. Provisional Application No. 62/991,940, filed Mar. 19, 2020, and entitled "Glenosphere Extractor," the entire disclosure of which is hereby incorporated by reference for all purposes.

BACKGROUND OF THE DISCLOSURE

The exemplary embodiments of present invention relate generally to a surgical extraction tool and, more specifically, to a tool for extracting an implant from bone including, without limitation, a glenosphere implant.

Implant extractor tools, including those used to extract a glenosphere from bone, are typically either simple mechanical devices that do not effectively grip the implant or complex mechanical devices that may effectively grip the implant but are expensive to manufacture and difficult to operate.

BRIEF SUMMARY OF THE DISCLOSURE

In accordance with an exemplary embodiment there is provided an implant extractor comprising a second arm having a proximal end and a distal end, and a first arm having a proximal end for attachment to an extraction device. The first arm additionally has a distal end for attachment to a first jaw, and an adjustment mechanism including an adjuster and a lever. The lever has a proximal end engaged with the adjuster and a distal end pivotably connected to the second arm. The implant extractor additionally comprises a link pivotably connected to the first and second arms, the link having a distal end for attachment to a second jaw.

According to an aspect, the implant extractor further comprises a biasing member biasing the link and the first arm. According to another aspect, the adjuster comprises a rotatable knob, and a rod extending from the rotatable knob and movable relative to the rotatable knob. According to another aspect, the rod is a threaded rod threadedly engaged with the first arm. According to another aspect, the rod includes at least one planar side. According to another aspect, the rotatable knob has an opening with a planar side to cooperate with the planar side of the rod. According to another aspect, the rod abuts the proximal end of the lever. According to another aspect, the first arm includes a cage having an opening for housing the rotatable knob. According to another aspect, the first arm includes a slot to house the rod. According to another aspect, the first arm includes a quick connect about its proximal end.

According to another aspect, the implant extractor further comprises a first jaw releasably attachable to the distal end of the first arm and a second jaw releasably attachable to the distal end of the link. According to another aspect, the first and second jaws each include a slidable lock to slidingly engage a corresponding slidable lock on the first arm and link, respectively. According to another aspect, the corresponding slidable lock on the first arm and link each includes a stop. According to another aspect, the stop on the first arm is a laterally extending stop and the stop of the link is a laterally extending stop. According to another aspect, the slidable lock is a dovetail. According to another aspect, the slidable lock on each of the first and second jaws is a male dovetail and the corresponding slidable lock on each of the first arm and the link is a female dovetail.

According to another aspect, the implant extractor further comprises a detent carried by one of the first jaw and the first arm, or a detent carried by one of the second jaw and the link. According to another aspect, the implant extractor further comprises a locking mechanism on the link movable between a locked position and an unlocked position, wherein in the locked position the locking mechanism maintains clamping engagement of the first and second jaws, and in the unlocked position the locking mechanism permits release of the first and second jaws from clamping engagement with an implant to be extracted. According to another aspect, the implant extractor further comprises a release lever on the second arm to release of the first and second jaws from clamping engagement with an implant to be extracted.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

FIG. 8D is a cross-sectional side view of the first arm of FIG. 8A;

FIG. 8E is a phantom line side view of the first arm of FIG. 8A including a threaded rod threadedly engaging the first arm;

FIG. 14 is a rear perspective view of a first jaw of the implant extractor of FIG. 1;

FIG. 15 is a rear perspective view of a second jaw of the implant extractor of FIG. 1;

FIG. 20A is a side view of an alternative configuration of the first jaw of the implant extractor of FIG. 1;

FIG. 20B is a perspective view of the alternative configuration of the first jaw of FIG. 20A;

FIG. 20C is a perspective view of the alternative configuration of the first jaw of FIG. 20A;

DETAILED DESCRIPTION OF THE DISCLOSURE

Figure 1:
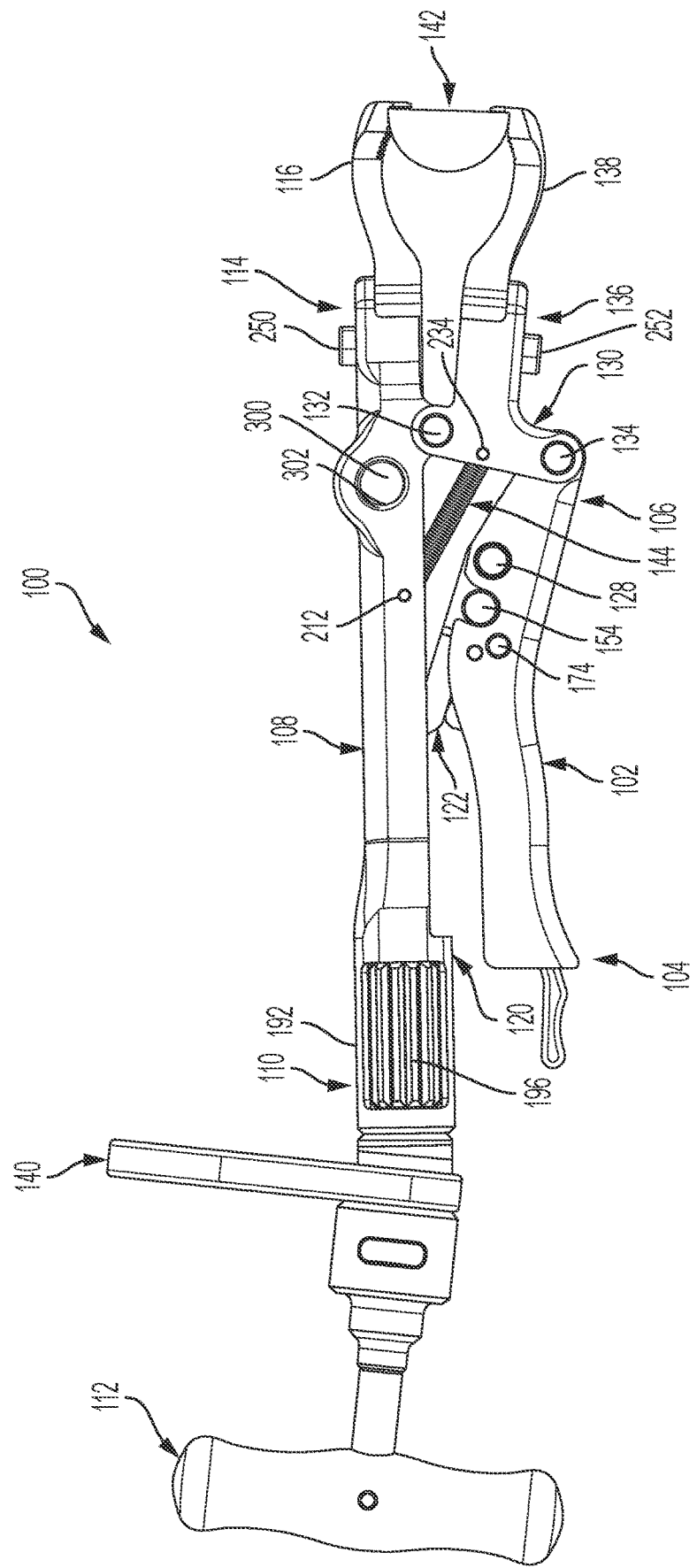
FIG. 1 is side view of an implant extractor in accordance with an exemplary embodiment of the subject disclosure.
Figure 2:
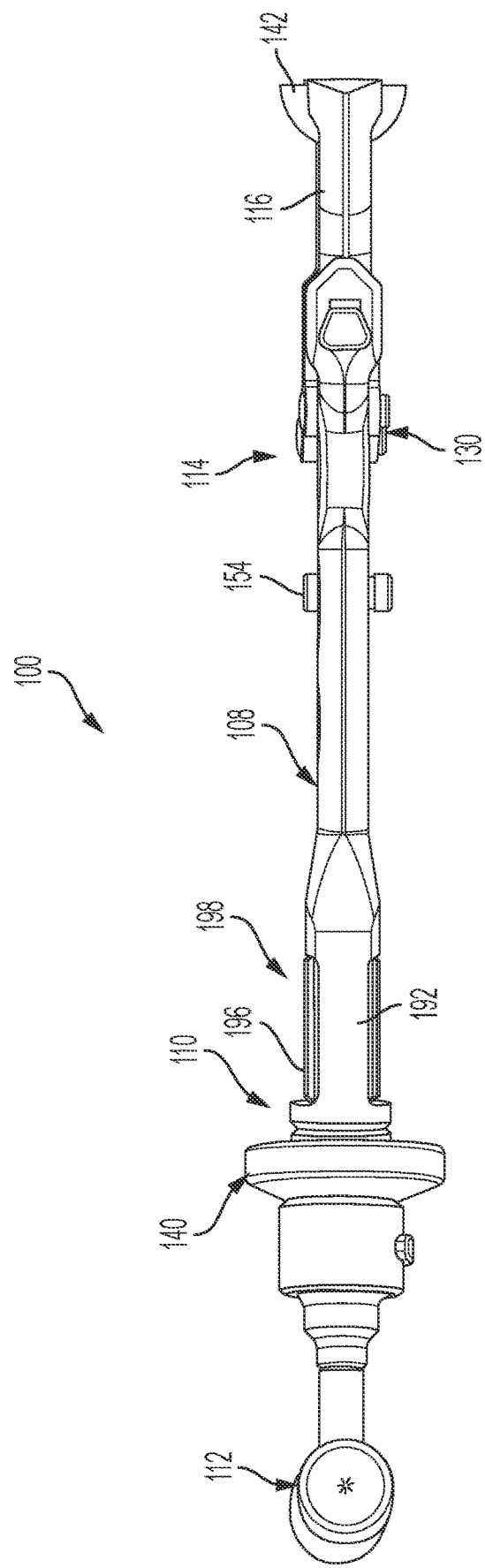
FIG. 2 is a posterior side view of the implant extractor of FIG. 1.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIGS. 1-3, 5 and 6 illustrate an implant extractor 100 in accordance with an exemplary embodiment of the present disclosure. The implant extractor 100 includes a second arm 102 having a proximal end 104 and a distal end 106, and a first arm 108 having a proximal end 110 for attachment to an extraction device 112. The extraction device 112 can be any suitable extraction device including, without limitation, a T-handle. The first arm additionally has a distal end 114 for attachment to a first jaw 116, and an adjustment mechanism 118 including an adjuster 120 and a lever 122. The lever has a proximal end 124 engaged with the adjuster and a distal end 126 pivotably connected to the second arm 102 via pivot pin 128. The implant extractor 100 additionally comprises a link 130 pivotably connected to the first and second arms via pivot pins 132, 134, the link having a distal end 136 for attachment to a second jaw 138.

Figure 4A:
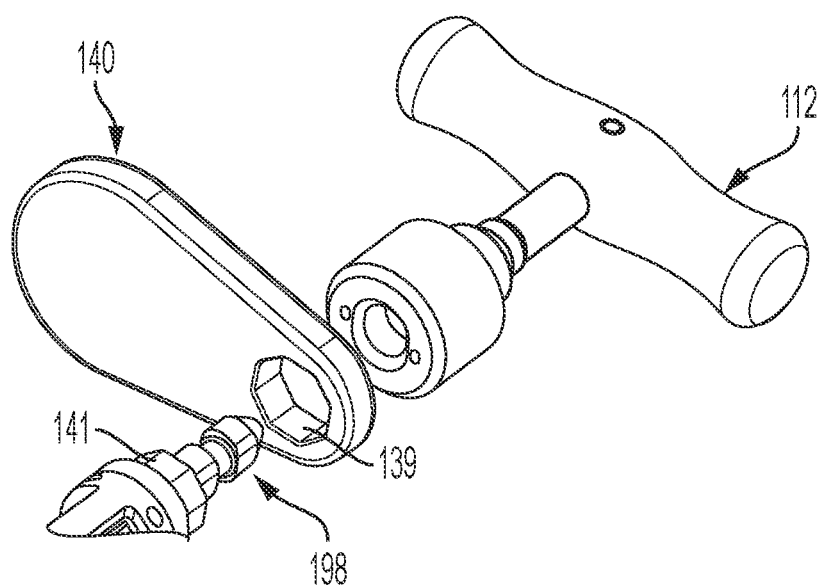
FIG. 4A is an exploded perspective view of an extraction device, strike plate and quick connect of the implant extractor of FIG. 1.
Figure 4B:
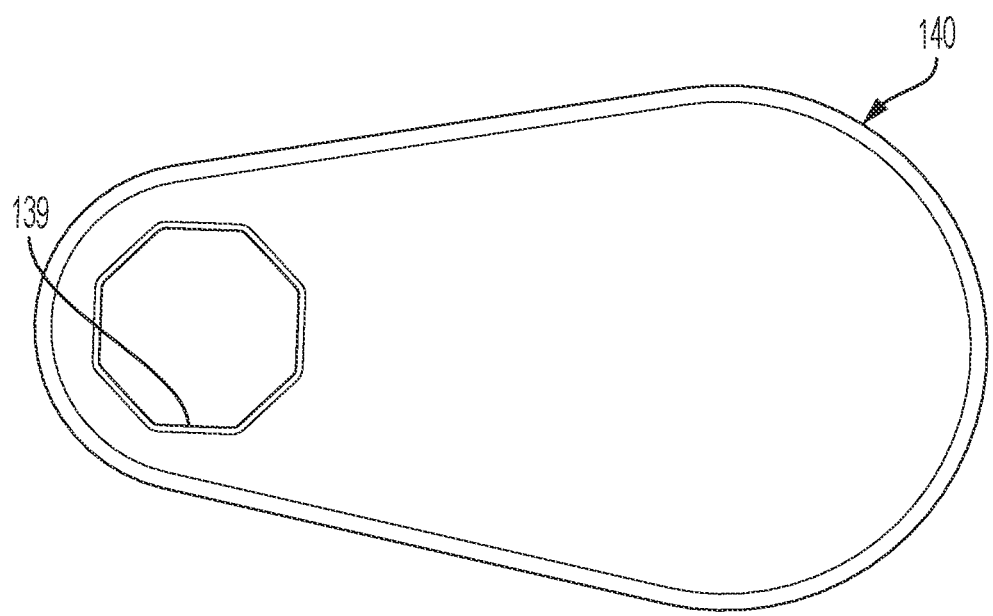
FIG. 4B is a plan view of a strike plate of the implant extractor of FIG. 1.

FIGS. 4A and 4B illustrate that the implant extractor can optionally include a planar laterally projecting strike plate 140 located adjacent the proximal end of the first arm. The strike plate includes a proximal face 140a and a distal face 140b and can include an opening e.g., a polygonal opening 139 for receiving a correspondingly shaped base e.g., polygonal base 141 of a quick connect 198, discussed below. So constructed, the strike plate may be rotatably positioned at different angles, and more specifically at different rotated angles about a longitudinal axis of the implant extractor or the implant extractor itself and set at an angle that is most appropriate and comfortable to the user for extraction. By way of example, the polygonal opening in the strike plate and the polygonal base 141 of the quick connect can be octagonal, whereby the strike plate may be placed in any one of eight positions about the implant extractor, or alternatively a polygonal base with a square, pentagon, hexagon, heptagon, nonagon, decagon, dodecagon shape or any number of sides corresponding in number to a plurality of sides of the polygonal opening. The extraction device 112 holds the strike plate 140 in place and both are easily removable from the quick connect 198.

Figure 7B:
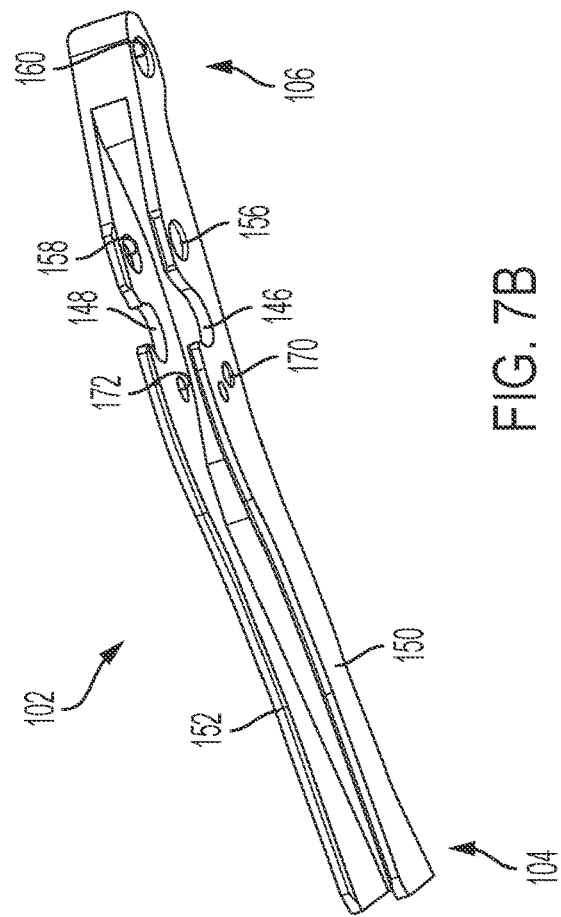
FIG. 7B is a perspective view of the second arm of FIG. 7A.
Figure 7A:
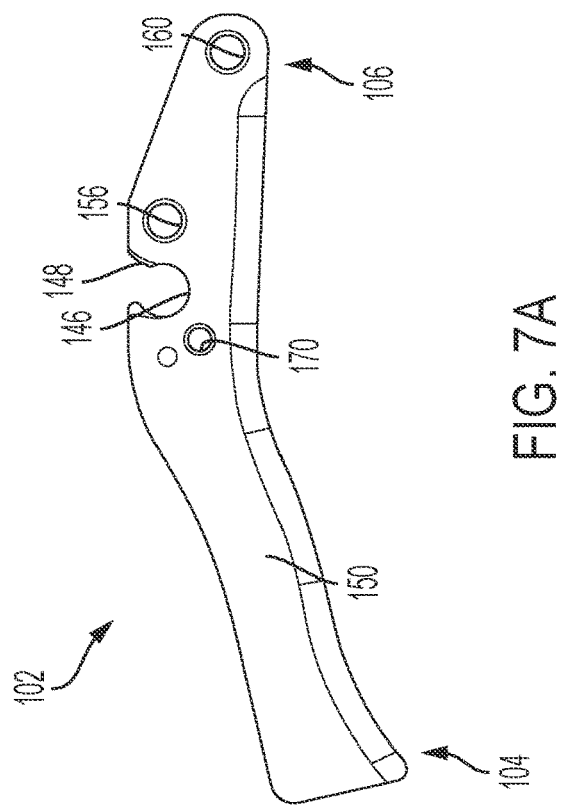
FIG. 7A is side view of a second arm of the implant extractor of FIG. 1.

The second arm 102 is configured as best shown in FIGS. 1, 7A and 7B, and is constructed as an elongated arm having a channel formed by upstanding sidewalls 150, 152. About its midportion the second arm is provided with a pair of notches 146, 148 in the upstanding side walls 150, 152 which are adapted to cooperate with a locking mechanism 154 (described below in connection with FIGS. 16 and 17) carried by the lever 122. The side walls 150, 152 further include a first pair of aligned openings 156, 158 that receive the pivot pin 128 for pivotably connecting the distal end 126 of the lever 122 to the second arm. About the distal end 106 of the second arm is a through bore 160 that aligns with aligned openings 162, 164 provided in the lower branches 166, 168 of the link 130 (FIGS. 12A-12C) to receive the pivot pin 134 to pivotably connect the distal end of the second arm 102 to the lower branches of the link. Additionally, the side walls 150, 152 include a second pair of aligned openings 170, 172 that receive a pivot pin 174 (FIGS. 1, 3, and 5) that likewise passes through a through bore 176 provided at a distal end 178 of a release lever 180 (FIG. 19) for pivotably connecting the distal end of the release lever to the second arm. The function of the release lever 180 is described in greater detail in connection with FIG. 19.

Figure 3:
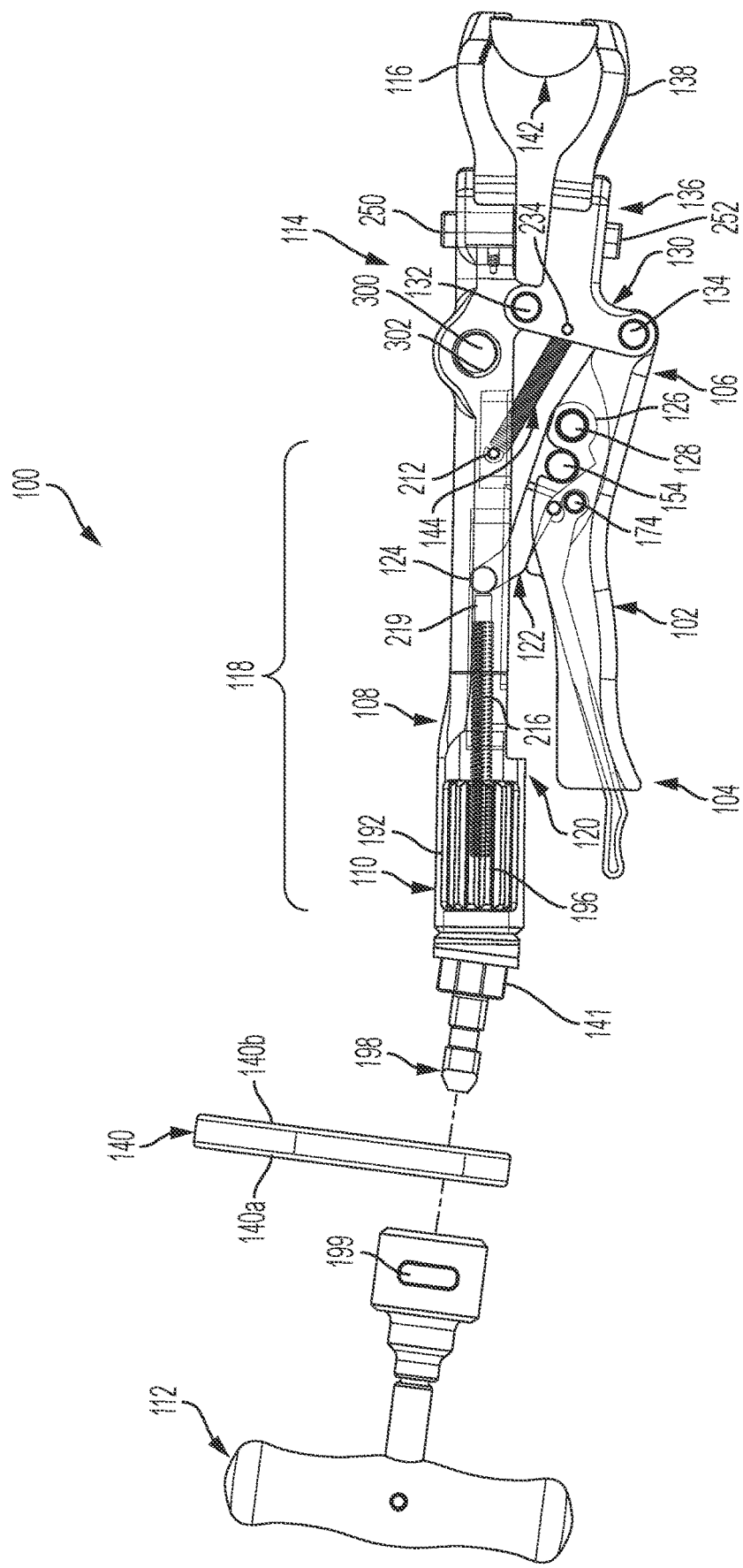
FIG. 3 is an exploded side view of the implant extractor of FIG. 1 with certain elements shown in phantom line for purposes of clarity.
Figure 5:
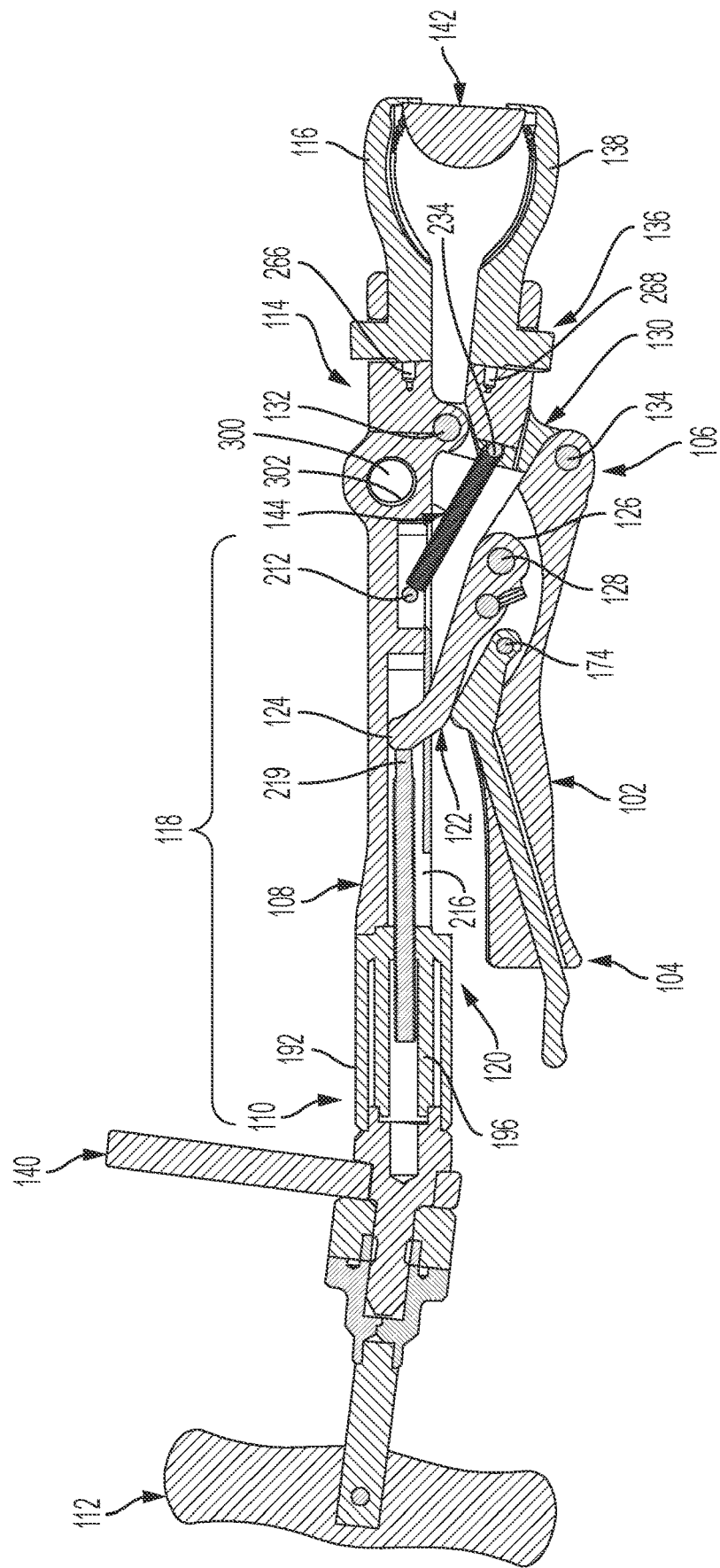
FIG. 5 is a partial cross-sectional side view of the implant extractor of FIG. 1.
Figure 8A:
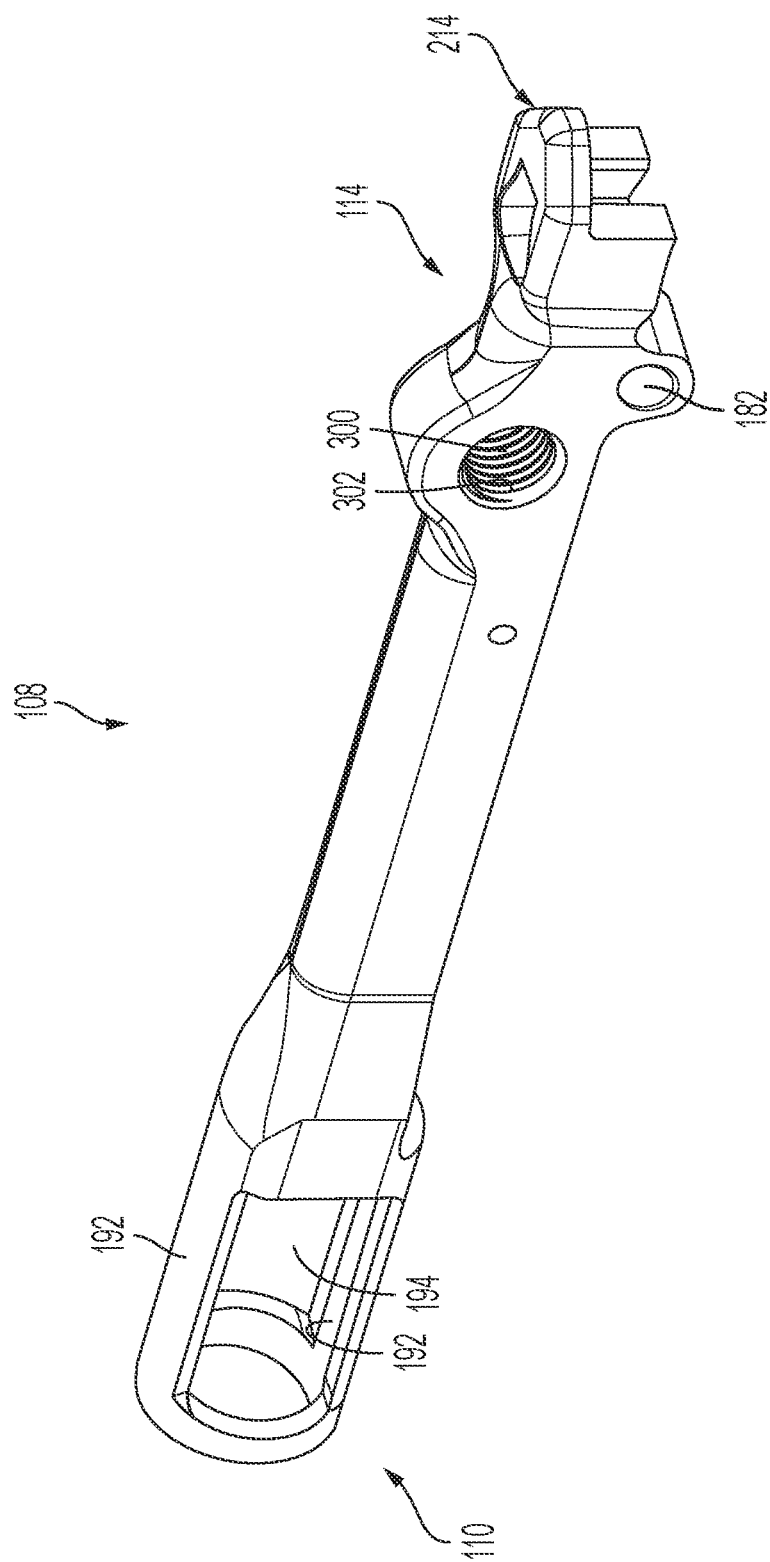
FIG. 8A is a rear perspective view of a first arm of the implant extractor of FIG. 1.
Figure 8B:
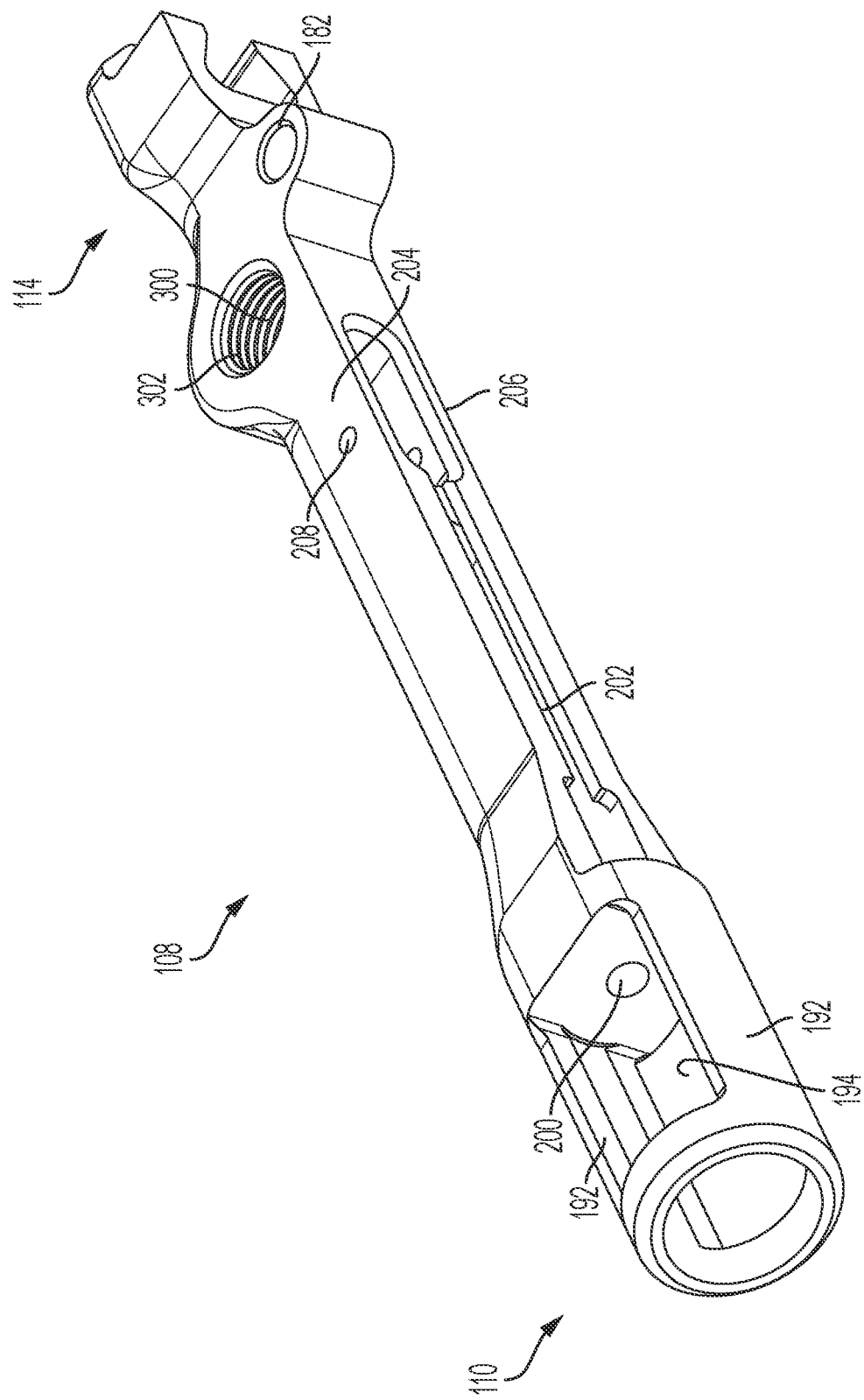
FIG. 8B is a front perspective view of the first arm of FIG. 8A.
Figure 8C:
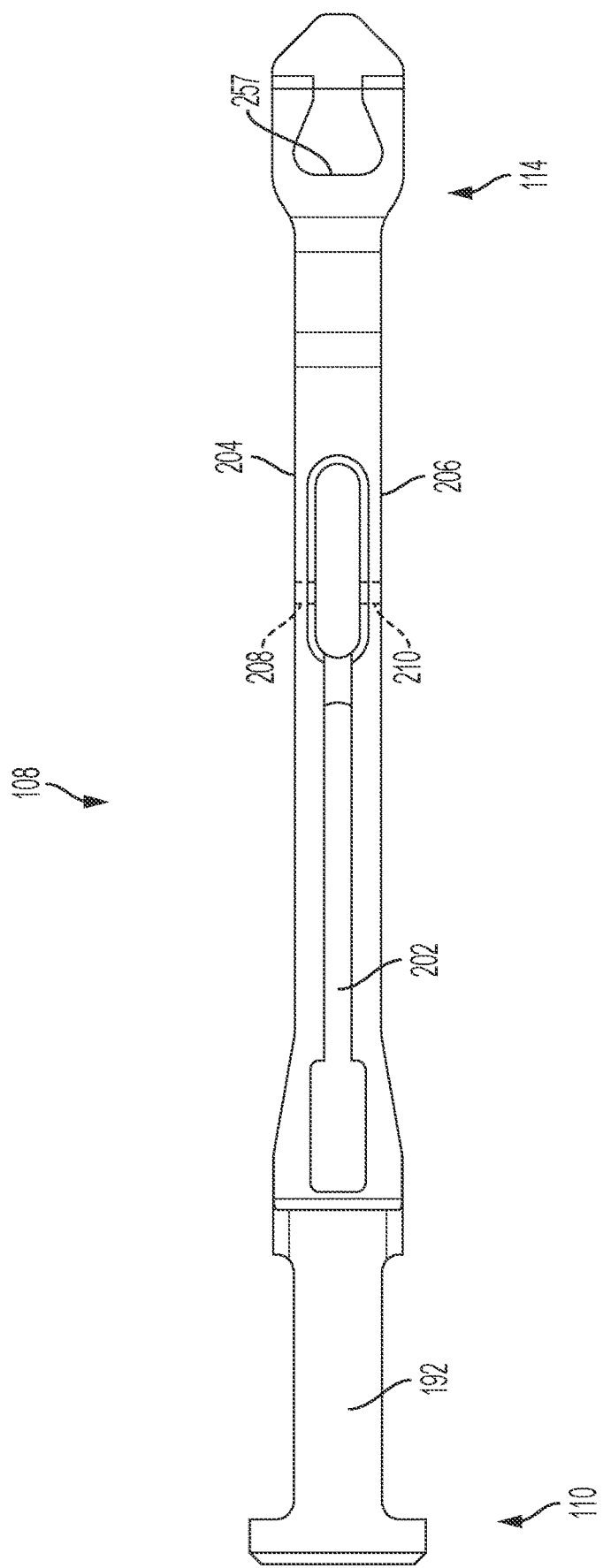
FIG. 8C is a bottom view of the first arm of FIG. 8A.

The construction of the first arm 108 is configured as best shown in FIGS. 1, 3, 5 and 8A-8E. FIGS. 8A-8E show a first arm body 109 of the first arm. Adjacent the distal end 114 of the first arm body there is provided a through bore 182 that aligns with aligned openings 184, 186 provided in the upper branches 188, 190 of the link 130 (FIGS. 12A-12C) to receive the pivot pin 132 to pivotably connect the distal end of the first arm 108 to the upper branches of the link. Also adjacent the distal end of the first arm body is a transverse opening 300 which includes fastener structure 302 configured to releasably retain various forms of extraction devices which are described in greater detail hereinafter. Near the proximal end 110, the first arm body includes a cage 192 having an opening or hollow interior 194 for housing a rotatable knob 196 which forms part of the adjuster 120 of the adjustment mechanism 118 (see also FIGS. 1, 3, 5 and 10A). Adjacent a distal end of the cage 192 is an internally threaded through bore 200 (FIGS. 8B, 8D and 8E). The through bore 200 is in fluid communication with the cage 192 and with a slot 202 (FIGS. 8C-8F) structured to house a rod 216, as further discussed below. Adjacent the slot 202 the first arm body includes a pair of side walls 204, 206 that is provided with aligned openings 208, 210 (FIGS. 8B and 8C) to receive a pin 212 which holds a first end of a biasing member 144 (FIGS. 1, 3, and 5). As shown in FIG. 8A, at the tip of the distal end 114, the first arm includes a slidable lock 214 for attachment to the first jaw 116, which is discussed in further detail below.

The first arm also includes the quick connect 198 (FIG. 3) about its proximal end structured to releasably engage with, e.g., a corresponding female quick connection carried by the extraction device 112. The corresponding female quick connection includes a biased locking member 199.

Figure 9B:
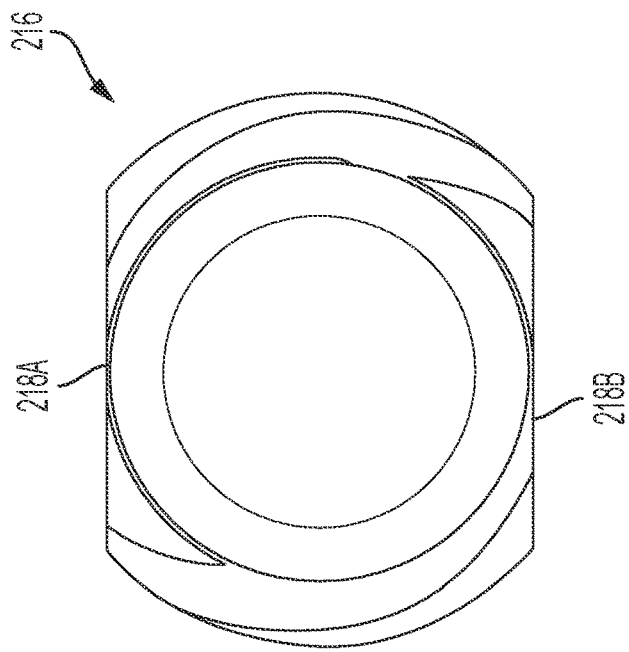
FIG. 9B is an end view of the threaded rod of FIG. 9A.
Figure 9A:
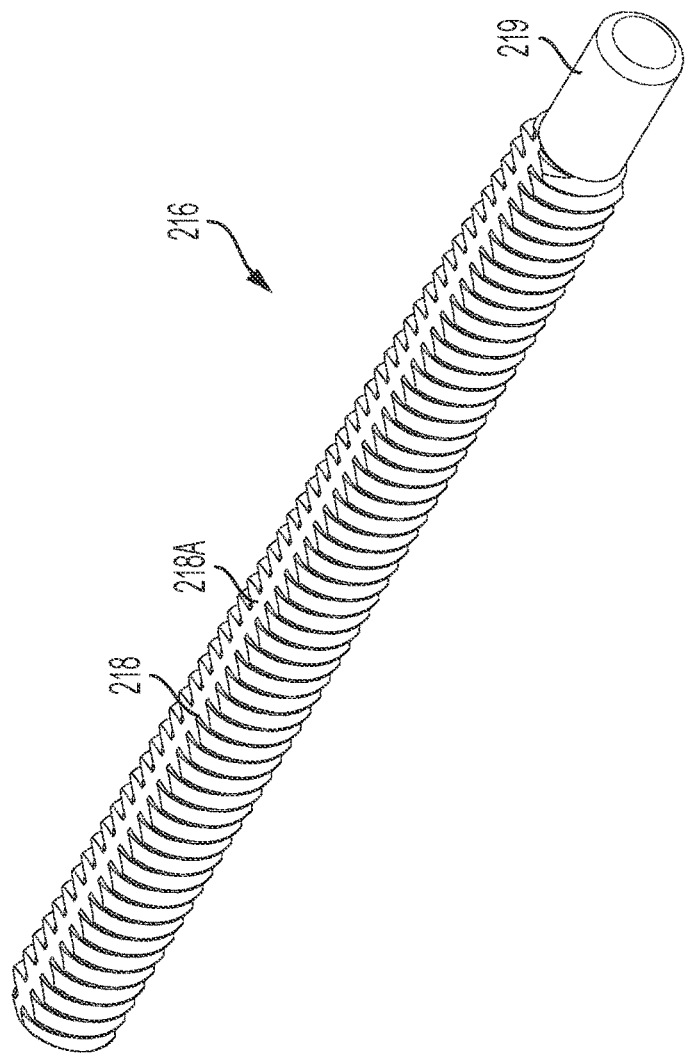
FIG. 9A is a perspective view of a threaded rod of an adjuster of the implant extractor of FIG. 1.

FIGS. 3 and 5 best illustrate the adjustment mechanism 118 of the first arm 108. The adjustment mechanism includes the adjuster 120 and the lever 122. The adjuster comprises the rotatable knob 196 and the rod 216. The rod 216 extends from the rotatable knob and is movable relative to the rotatable knob. The rod 216 is a threaded rod (FIGS. 8E, 9A and 9B) threadedly engaged with the first arm at the internally threaded through bore 200 as shown in FIG. 8E. The rod 216 includes at least one planar side 218, and preferably a pair of opposing planar sides 218A, 218B. The rod also includes a non-threaded distal nose 219. The rod is sized in length sufficiently such that the distal nose 219 of the rod 216 abuts the proximal end 124 of the lever 122.

Figure 10B:
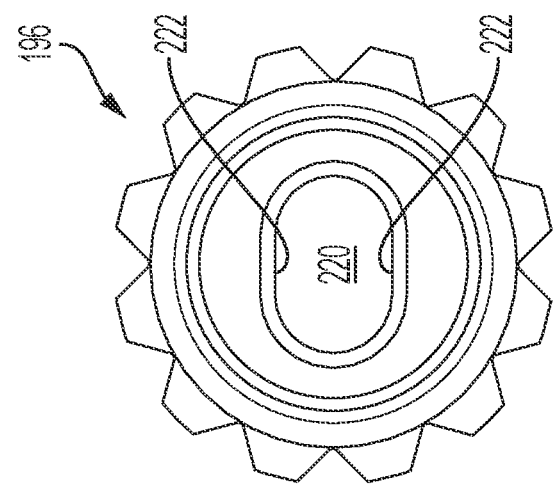
FIG. 10B is an end view of the rotatable knob of FIG. 10A.
Figure 10A:
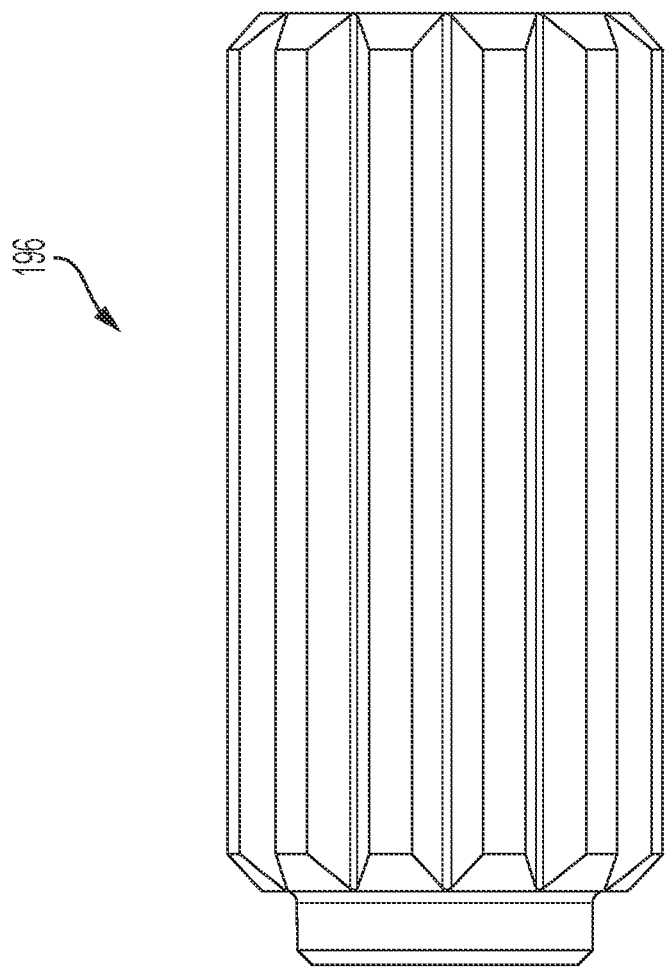
FIG. 10A is a side view of a rotatable knob of an adjuster of the implant extractor of FIG. 1.

The rotatable knob 196 is configured as best shown in FIGS. 10A and 10B having a generally cylindrical configuration. The outer surface of the rotatable knob is preferably textured, e.g. with splines, knurling or the like, to enhance gripping of a user's fingers when rotating the rotatable knob. As shown in FIG. 10B, the rotatable knob 196 has an opening 220 about its end or proximally facing end, with a planar side 222 to cooperate with the planar side 218 of the rod 216. Rotation of the rotatable knob 196 causes rotation of the threaded rod 216 within the internally threaded through bore 200, thereby causing the rod 216 to extend from or retract into the rotatable knob depending on the direction of rotation of the rotatable knob, or in other words move along a direction of a longitudinal axis of the rod. More particularly, rotation of the rotatable knob 196 in a first direction causes the rod 216 to extend from the rotatable knob. In so doing, the distal nose 219 of the rod pushes further against the proximal end 124 of the lever 122. Conversely, rotation of the rotatable knob 196 in a second direction causes the rod 216 to retract into the rotatable knob. In so doing, the proximal end 124 of the lever 122 remains in contact with the distal nose 219 of the rod 216 since it is under the influence of the biasing member 144, discussed below.

Figure 6:
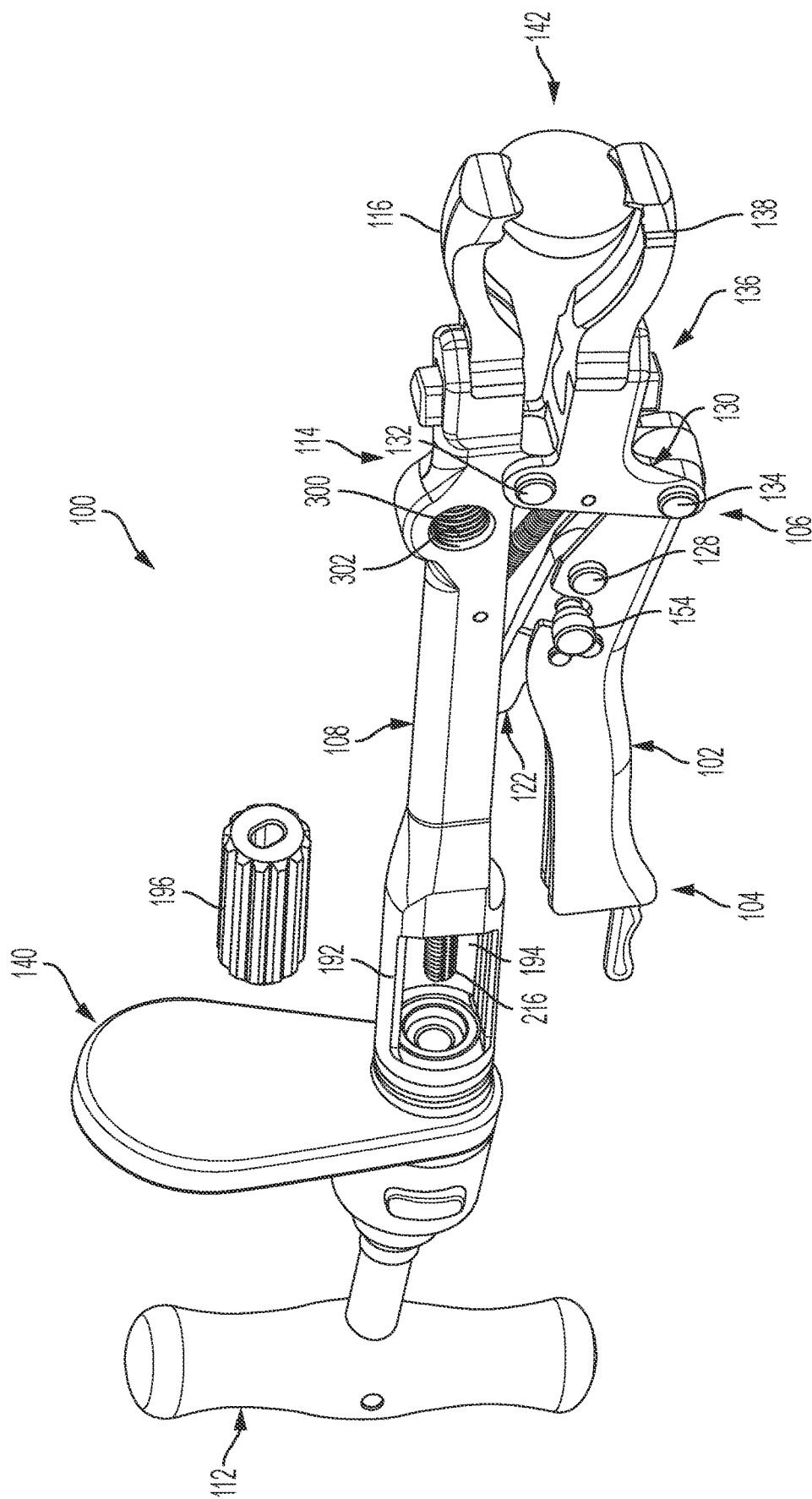
FIG. 6 is a rear perspective view of the implant extractor of FIG. 1 with a rotatable knob shown separated from the implant extractor.
Figure 11:
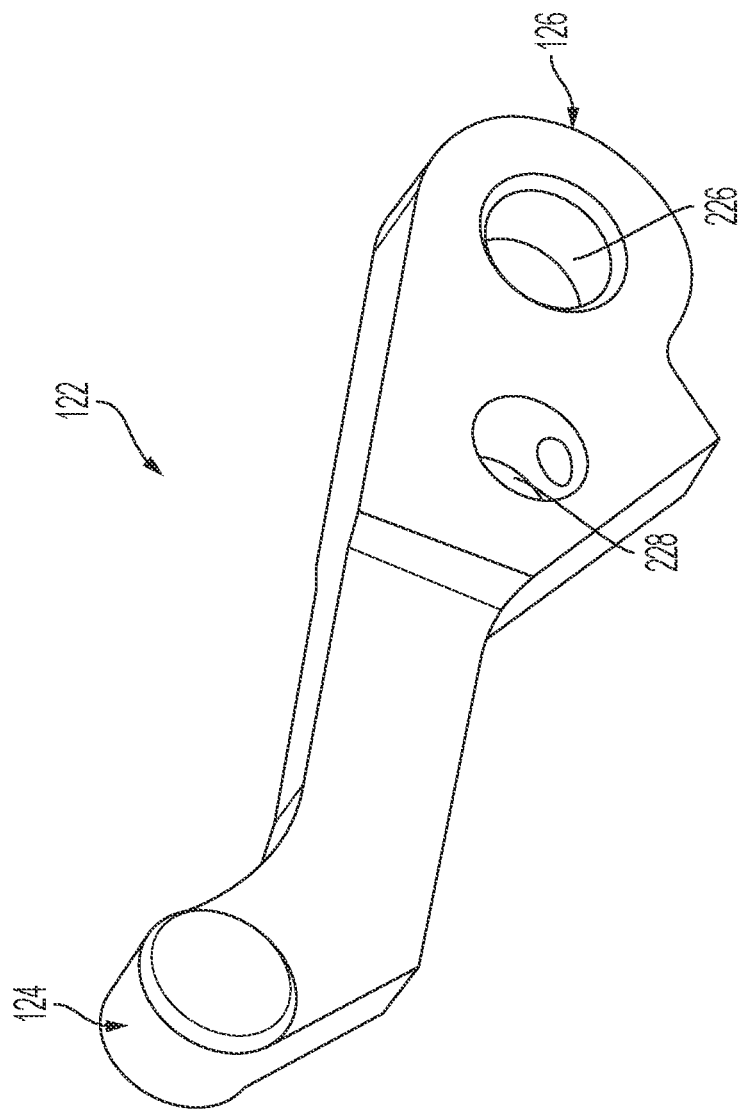
FIG. 11 is a left perspective view of a lever of the implant extractor of FIG. 1.

The lever 122 is structured as best shown in FIGS. 1, 5 and 11. Referring to FIG. 11, between its proximal and distal ends 124, 126, the lever 122 includes a first through bore 226 that receives the pivot pin 128 for pivotably connecting the distal end 126 of the lever 122 to the second arm (FIGS. 3, 5 and 6). The lever 122 further includes a second through bore 228 through which the locking mechanism 154 passes (see FIGS. 1-3, 6 and 16).

Figure 12C:
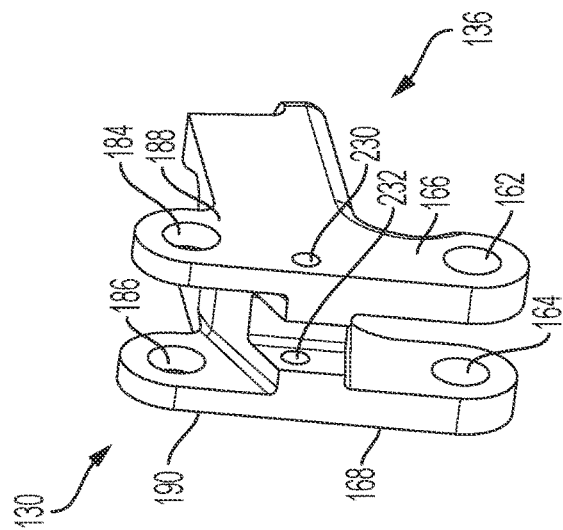
FIG. 12C is a rear perspective view of the link of FIG. 12A.
Figure 12B:
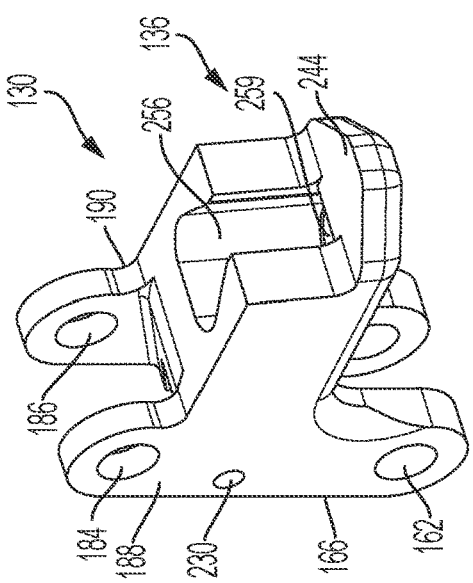
FIG. 12B is a front perspective view of the link of FIG. 12A.
Figure 12A:
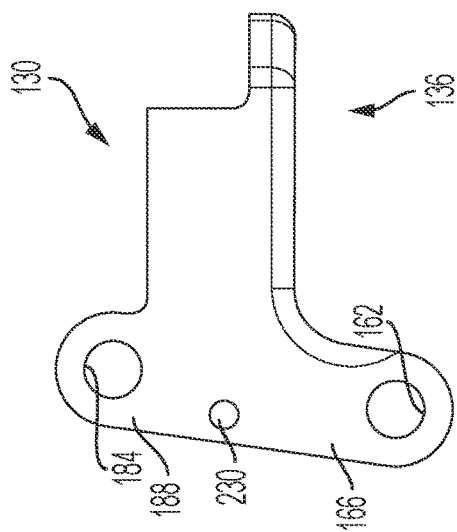
FIG. 12A is a side view of a link of the implant extractor of FIG. 1.

FIGS. 12A-12C best show the construction of the link 130. The link includes upper and lower branches. Between the upper branches 188, 190 and lower branches 166, 186, the link includes a pair of aligned through bores 230, 232. The through bores 230, 232 receive a pin 234 which holds a second end of the biasing member 144 (FIGS. 1, 3, and 5). The distal end 136 of the link 130 is provided with a fastener 256 for attaching the second jaw 138 to the link. Likewise, the distal end 114 of the first arm 108 is provided with a fastener 254 for attaching the first jaw 116 to the first arm. As shown in FIG. 12B the link includes an aperture 259 for receiving a mail dovetail 252 of the second jaw 138. As a result the first jaw is releasably attachable to the distal end of the first arm via engagement of a male dovetail 250 of the first jaw with an aperture 257 of the first arm and the second jaw is releasably attachable to the distal end of the link via engagement of the male dovetail 252 with the link aperture 259.

The fasteners at the distal ends of the link and the first arm are preferably cooperating fasteners or slidable locks that respectively engage cooperating fasteners or cooperating slidable locks provided at the proximal ends of the first and second jaws.

The implant extractor 100 further comprises the aforementioned biasing member 144 which is connected to and biases the link 130 and the first arm 108, in a manner described in greater detail below. The biasing member can be e.g., a tension spring, an elastomer or the like. In the present embodiment, the tension spring has a spring constant of about 0.5 to 8.0 lbs, including 0.4, 0.6, 0.7, 0.8, 0.9, 1.0, 2.0, 3.0, 4.0, 5.0, 6.0, 7.0, and 9.0 lbs.

Figure 13:
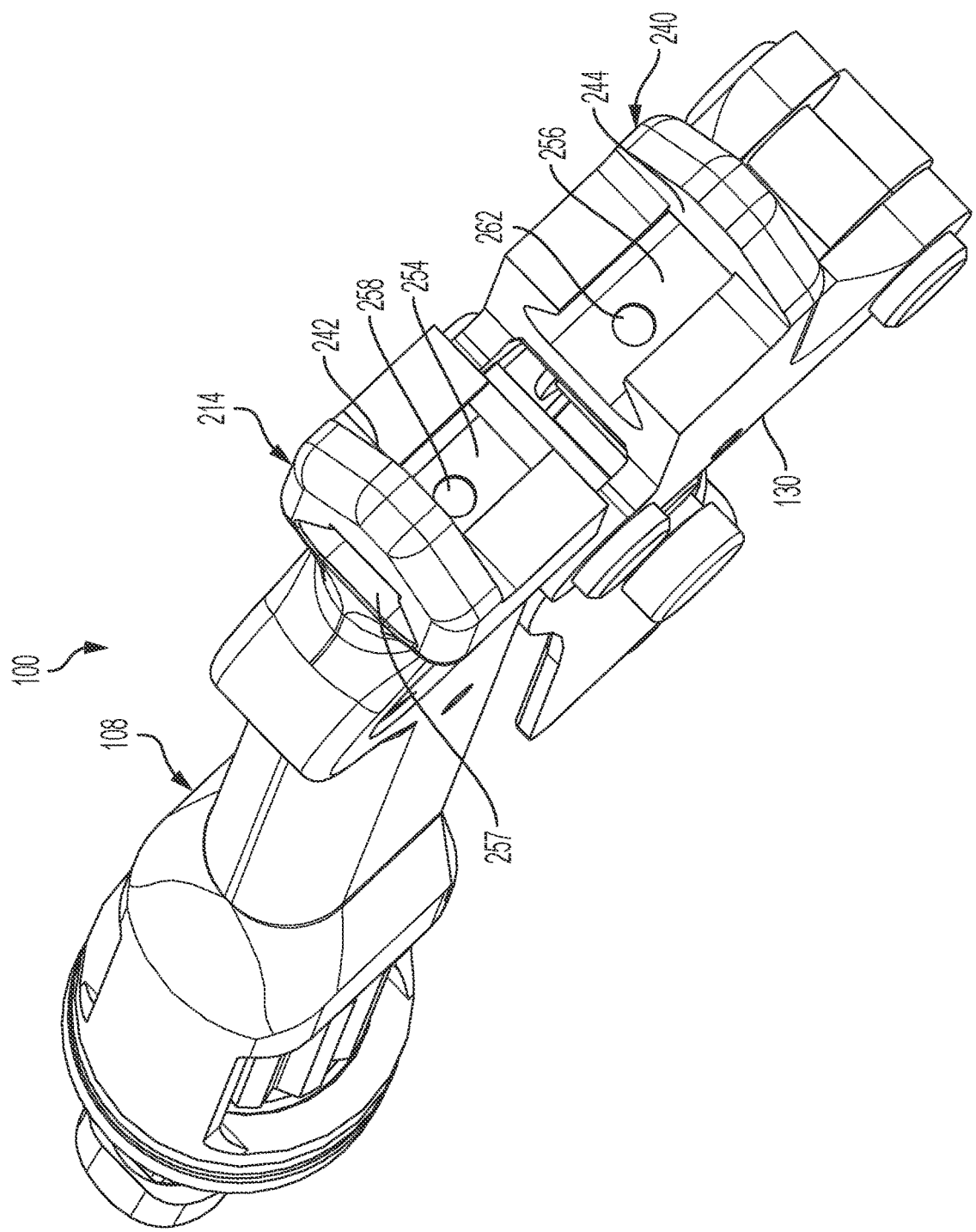
FIG. 13 is a rear perspective of the implant extractor of FIG. 1 with first and second jaws thereof omitted for purposes of clarity.

The first and second jaws respectively are structured as best shown in FIGS. 14 and 15. The first and second jaws respectively include a corresponding recess 260 and 264 to releasably engage respective corresponding detents 258, 262 (FIG. 13) on the distal ends of the first arm and the link. The first and second jaws respectively include slidable locks 236 and 238 to slidingly engage a corresponding slidable lock 214, 240 on the first arm 108 and link 130, respectively, as shown in FIG. 13. Still referring to FIG. 13, the corresponding slidable locks on the first arm and link each includes a stop 242, 244. According to an aspect, the stops 242, 244 are distally extending ledges. The stops 242, 244 are engageable by flats 246, 248 respectively provided on the first and second jaws (FIGS. 14 and 15) to limit insertion of the first and second jaws into the first arm and the link.

According to another aspect, the slidable lock 236 and 238 on each of the first and second jaws is the male dovetail 250 and 252, respectively (FIGS. 14 and 15), and the corresponding slidable lock 214, 240 on each of the first arm and the link is a female dovetail 254 and 256, respectively (FIG. 13). The first and second jaws are thus inserted from inner or medial sides of the first arm and the link towards their outer or lateral sides thereof, whereby the flats 246, 248 stop the slidable locks from further insertion upon engagement with the stops 242, 244. Additionally, the male dovetails 250, 252 of the jaws have longitudinal lengths whereby, when inserted into the female dovetails 254, 256, the male dovetails project outwardly of the first arm and the link, as shown in FIGS. 1 and 3.

According to another aspect, the implant extractor further comprises a detent 258 (FIG. 13) carried by one of the first jaw and the first arm, or a detent 262 carried by the one of the second jaw and the link. In the illustrated exemplary embodiment, the detent 258 is carried by the first arm for engaging a corresponding recess 260 in the first jaw, and the detent 262 is carried by the link for engaging corresponding recess 264 in the second jaw (FIGS. 13-15). An exemplary detent can be e.g., a ball detent. As shown in FIG. 5, the detents 258, 262 are urged outwardly toward engagement with recesses 260, 264 by biasing members 266 and 268, such as springs or the like. Engagement of the detents with their corresponding recesses operates to resist inadvertent dislodgement of the first and second jaws from the first arm and the link. When it is desired to release the jaws from the first arm and the link, the user presses against the outwardly projecting male dovetails 250, 252 with sufficient force to overcome the biasing force of the biasing members 266, 268, whereby the detents become dislodged from the recesses.

Figure 16:
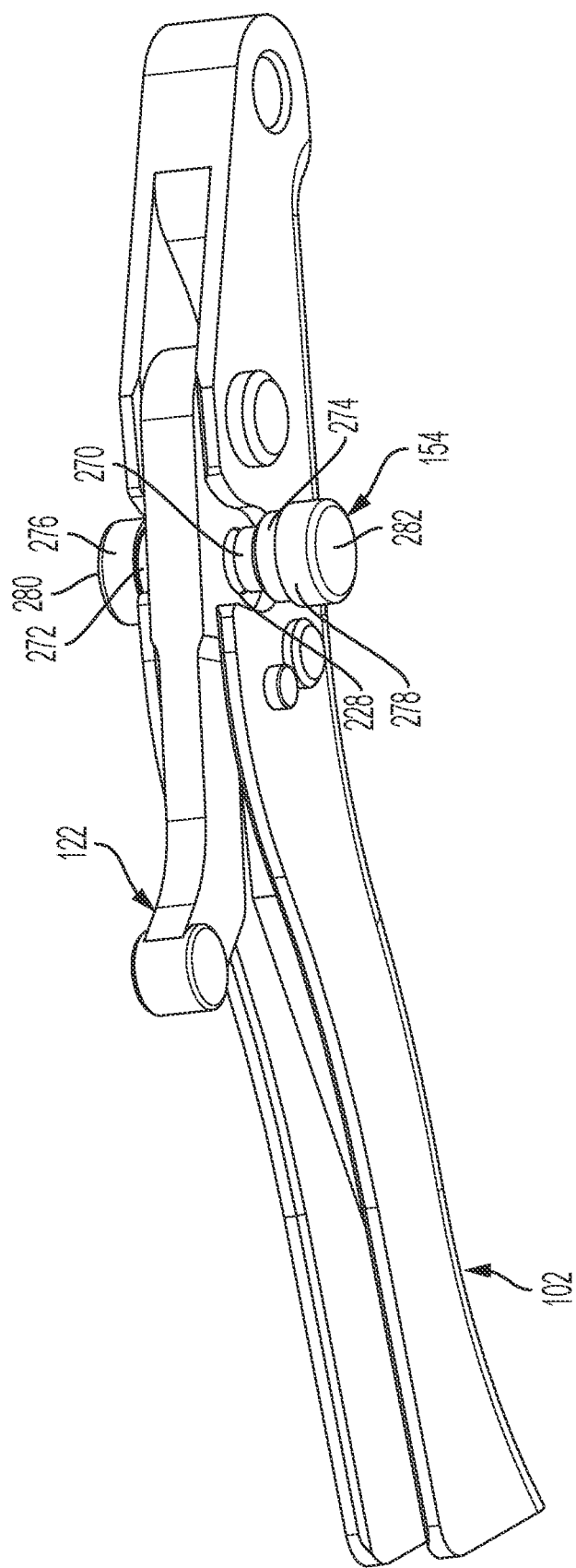
FIG. 16 is a perspective view of the lever, the second arm and the locking mechanism of the implant extractor of FIG. 1 in an unlocked position.
Figure 17:
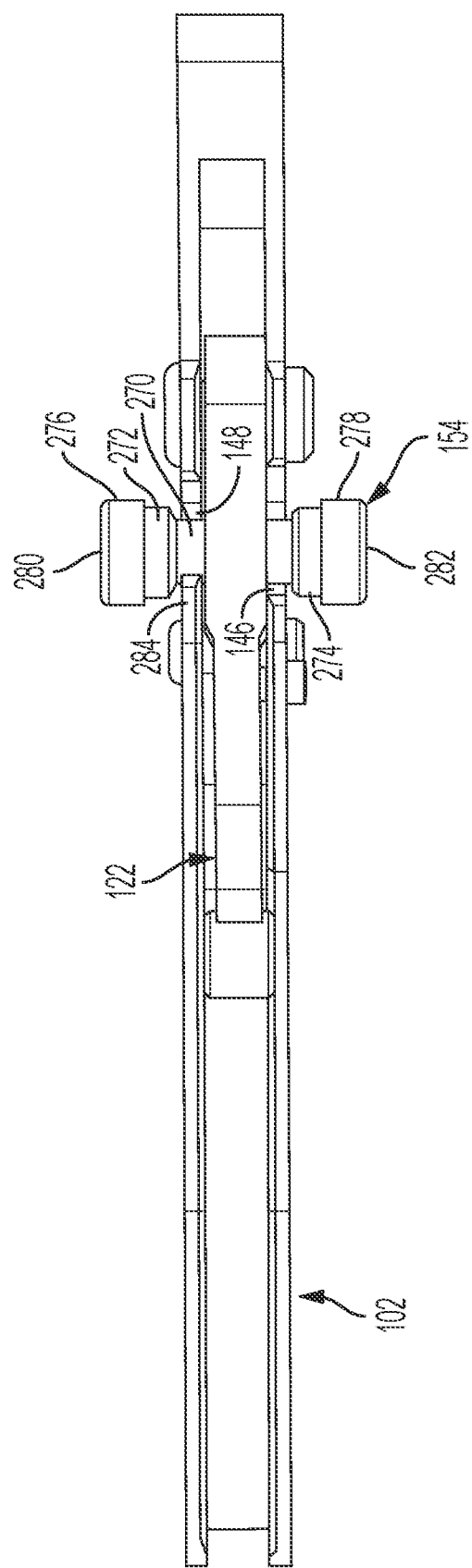
FIG. 17 is a top view of the lever, the second arm and the locking mechanism of FIG. 16 in an unlocked position.
Figure 18:
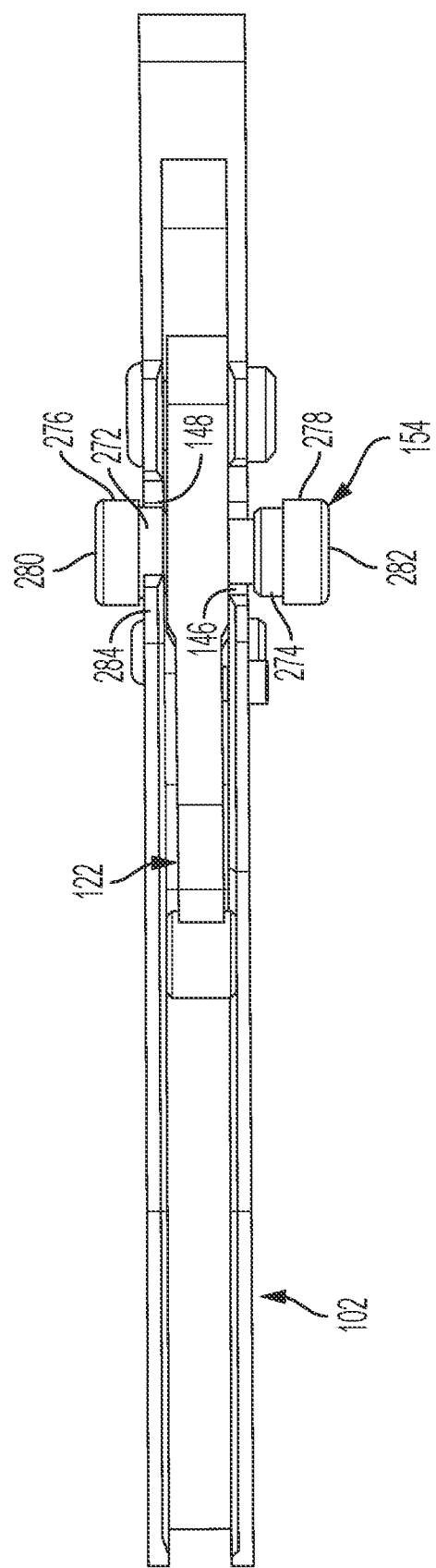
FIG. 18 is a top view of the lever, the second arm and the locking mechanism of FIG. 16 in a locked position.

The locking mechanism 154 is configured as best shown in FIGS. 16-18. The locking mechanism 154 is carried by the lever 122. That is, the locking mechanism is on the lever and movable between a locked position and an unlocked position. In the locked position (FIG. 18), the locking mechanism maintains clamping engagement of the first and second jaws and, in the unlocked position (FIGS. 16 and 17), the locking mechanism permits release of the first and second jaws from clamping engagement with an implant to be extracted.

The locking mechanism includes a central shaft 270 sized to reciprocate within the through bore 228 of the lever 122. At opposite ends of the central shaft 270, the locking mechanism includes first cylindrical portions 272, 274 of larger diameter than the central shaft that are sized to be received in notches 146, 148 provided in the upstanding side walls of the second arm 102. Additionally, adjacent the outside or lateral ends of the first cylindrical portions are second cylindrical portions or buttons 276, 278 of larger diameter than the first cylindrical portions. The outer surfaces 280, 282 of the buttons 276, 278 are adapted to be pressed by a user's finger.

To place the locking mechanism 154 into the locked position, the user presses the outer surface 280 of the button 276 until the first cylindrical portion 272 is received in notch 148 (FIG. 18). The notch 148 includes an overhang 284 which overlies the first cylindrical portion 272. The overhang prevents dislodgement of the cylindrical portion 272 from the notch 148 and secures the second arm 102 and the lever 122 connected thereto into a locked position.

To place the locking mechanism 154 into the unlocked position, i.e., to release the locking mechanism from the locked position, a user presses the outer surface 282 of the button 278 until the first cylindrical portion 272 is no longer received in the notch 148 and retained by the overhang 284. With the locking mechanism 154 in such position, the user can separate the second arm from the first arm whereby the first and second jaws are released from clamping engagement with implant 142.

Figure 19:
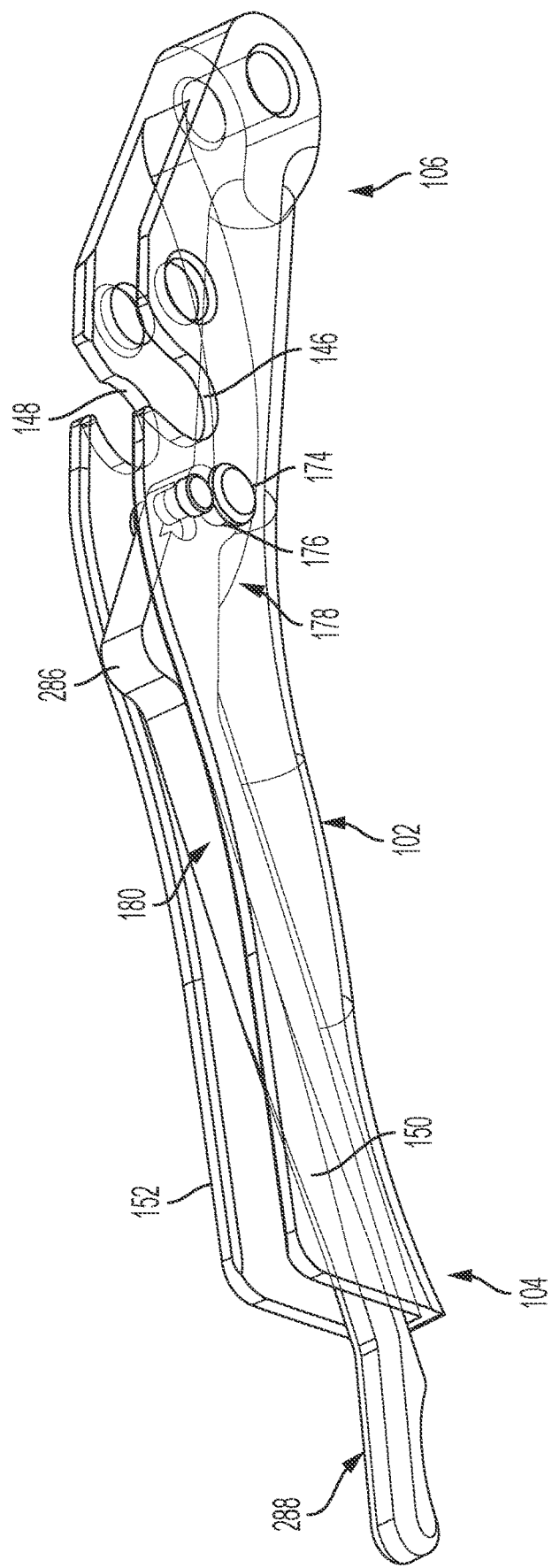
FIG. 19 is a perspective view of a release lever and the second arm of the implant extractor of FIG. 1 with the second arm shown in phantom line for purposes of clarity.
Figure 21B:
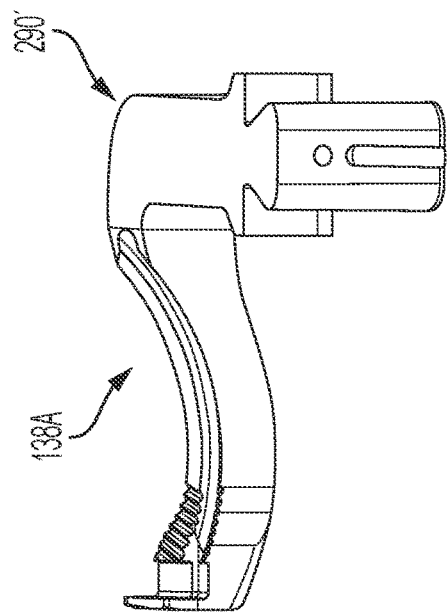
FIG. 21B is a perspective view of the alternative configuration of the second jaw of FIG. 21A.
Figure 21C:
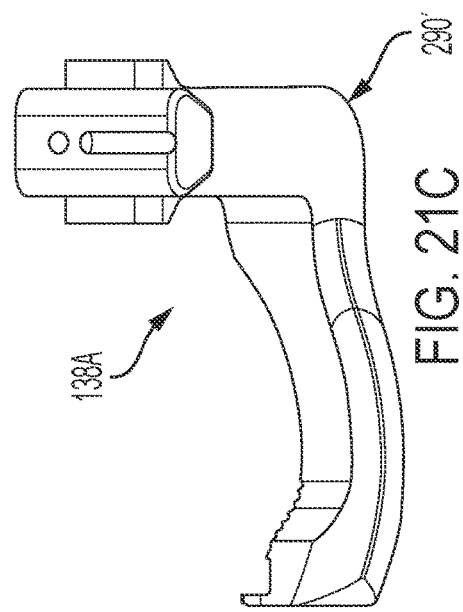
FIG. 21C is a perspective view of the alternative configuration of the second jaw of FIG. 21A.
Figure 21A:
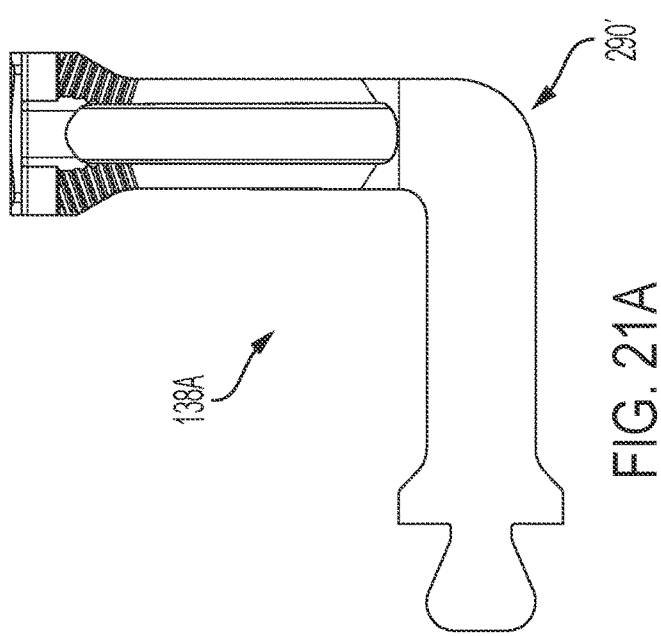
FIG. 21A is a side view of an alternative configuration of the second jaw of the implant extractor of FIG. 1.

The implant extractor 100 further comprises a release lever 180 (FIG. 19) on the second arm 102 to release the first and second jaws from clamping engagement with an implant to be extracted. The release lever has a knuckle 286 provided adjacent the distal end 178 thereof, and a proximal end 288 projecting from the proximal end 104 of the second arm. Before deploying the release lever, the user must place the locking mechanism 154 oriented in the unlocked position. The proximal end 288 of the release lever is lifted upwardly (as shown in FIG. 19) until the knuckle 286 contacts the underside of the lever 122. Further lifting of the release lever operates to withdraw the locking mechanism from the notches 146, 148 and push the second arm 102 away from the first arm 108, thereby allowing the first and second jaws to spread apart.

The first and second jaws 116, 138 heretofore discussed can be referred to as straight jaws in that the proximal ends of the jaws extend straight from the distal ends of the first arm and the link. FIGS. 20A-20C and 21A-21C illustrate an alternative exemplary configuration of the first and second jaws. The first and second jaws 116A, 138A illustrated can be referred to as laterally offset jaws. In this regard, intermediate regions of the first and second jaws 116A, 138A include laterally directed bend 290 and 290', respectively, whereby the distal ends of the jaws are laterally offset from the distal ends of the first arm and the link.

The first and second jaws 116, 138 (or 116A, 138A) are operable to releasably clamp a medical implant including, without limitation, e.g., a glenosphere implant 142.

Referring to the first and second jaws 116, 138 as an example, in order to clamp the first and second jaws onto an implant to be extracted, a user first rotates the rotatable knob 196 in a first direction which causes the first and second jaws to separate until opposed lips 292, 294 at respective distal ends of the first and second jaws (FIGS. 14 and 15) are spaced slightly wider than the circumference of the implant to be extracted. More particularly, rotation of the rotatable knob in the first direction causes the distal end 126 of the lever and the second arm 102 to move rearwardly, whereby the link 130 pivots rearwardly and the second jaw 138 moves away from the first jaw 116. The user then places the opposed lips adjacent the implant and rotates the rotatable knob in the opposite direction which causes the first and second jaws to close around the implant until the lips 292, 294 are positioned behind the implant. More particularly, rotation of the rotatable knob in the opposite direction causes the distal end 126 of the lever and the second arm 102 to move forwardly, whereby the link 130 pivots forwardly causing the second jaw 138 to move toward the first jaw 116. Additionally, the biasing member 144 keeps the first and second jaws open during clamping of the implant 142. That is, the biasing member serves to prevent the second jaw from uncontrolled movement which could hinder clamping of the first and second jaws to the implant. The user then squeezes the first and second arms together whereupon the second arm pivots posteriorly until the locking mechanism 154 becomes seated in the notches 146, 148 of the second arm. During seating of the locking mechanism into the notches, the first and second jaws are urged into tight clamping engagement with the implant 142. Once the locking mechanism is fully seated in the notches, the user presses the outer surface 280 of the button 276 until the first cylindrical portion 272 is received in the notch 148, thereby locking the position of the second arm relative to the first arm. With the second arm locked and the implant extractor 100 secured to the implant, the user may use the implant extractor to pull the implant from the bone to which it is attached. If additional force is necessary to extract the implant, the user may strike the distal face 140b of the strike plate 140 with a hammer, mallet or similar striking tool to dislodge the implant. Once the implant is freed, the user unlocks the locking mechanism 154 and lifts the proximal end 284 of the release lever to open the first and second jaws and release the implant from the implant extractor.

Figure 22A:
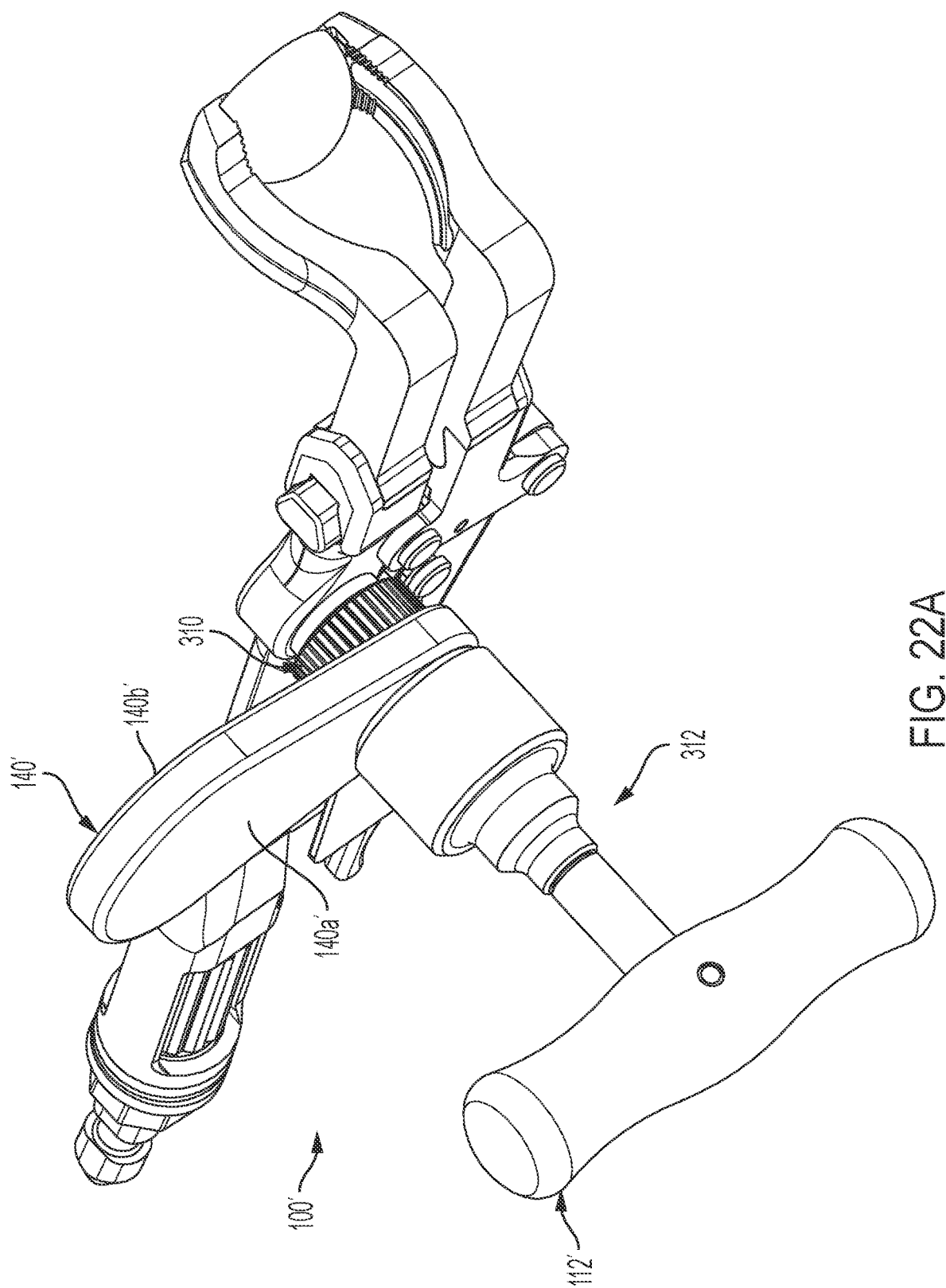
FIG. 22A is a bottom perspective view of an another exemplary embodiment of an of the implant extractor in accordance with the subject disclosure.
Figure 22B:
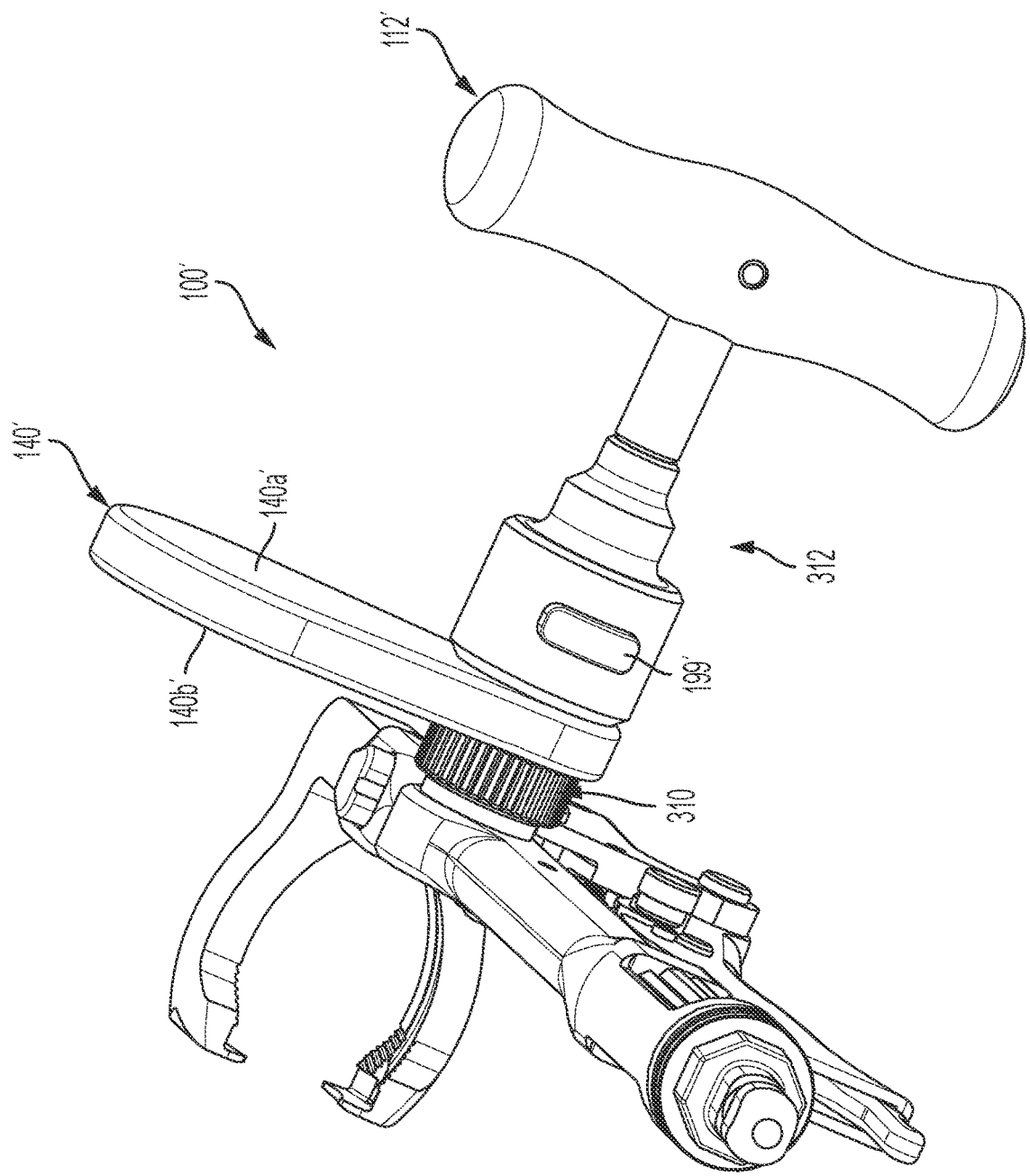
FIG. 22B is a top perspective view of the implant extractor of FIG. 22A.
Figure 22C:
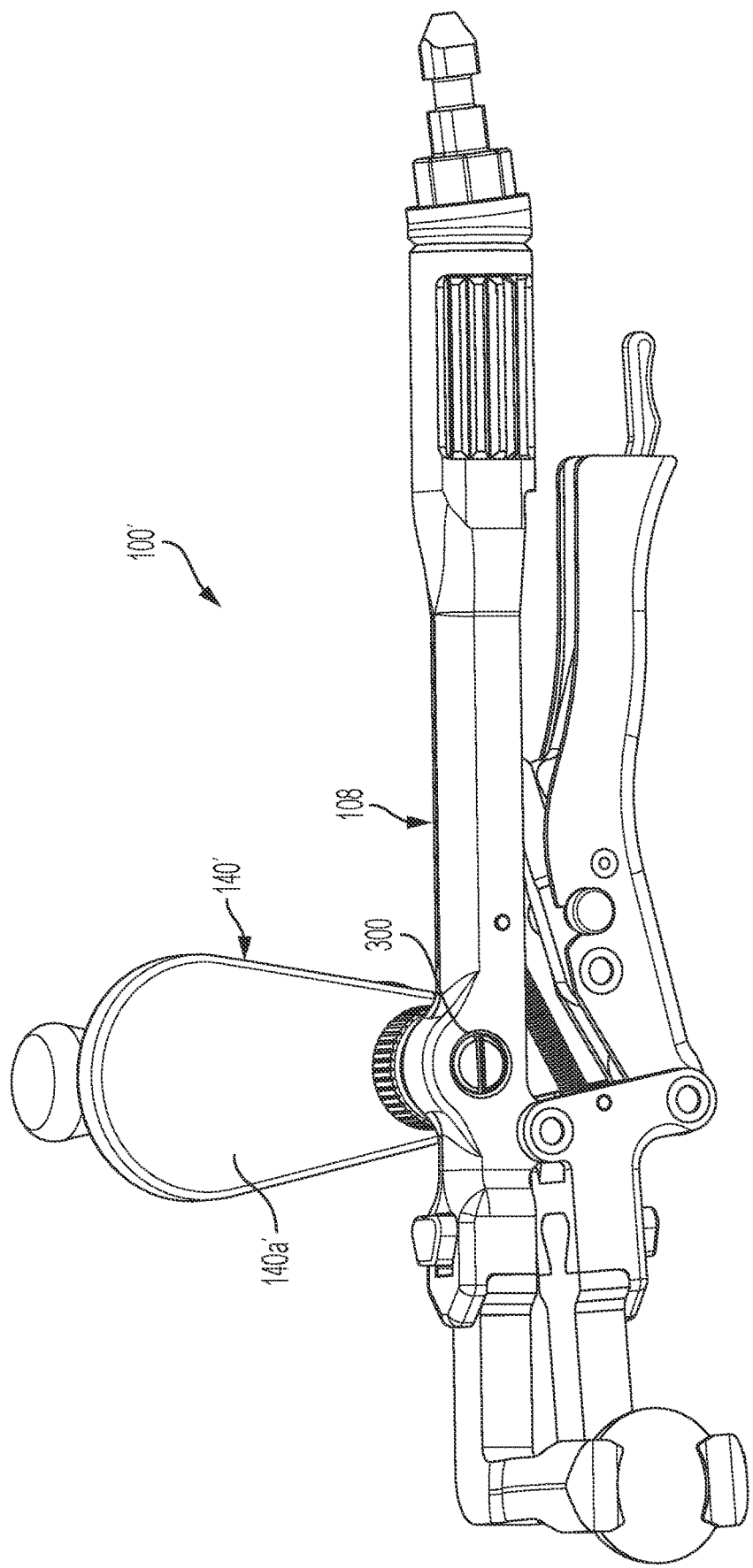
FIG. 22C is an side view of the implant extractor of FIG. 22A.

FIGS. 22A-22C show another exemplary embodiment of an implant extractor 100' according to the subject disclosure. In many respects, the implant extractor 100' is similar in construction to the implant extractor 100. Accordingly, for brevity only those aspects of the implant extractor 100' which materially depart in structure and/or function from the implant extractor 100 will be described in detail. In this regard, the implant extractor 100' comprises a connector member 310 (FIG. 23) constructed and arranged to releasably join an extraction device 312 to the fastener structure of the transverse opening 300 in the first arm 108. In the illustrated example of FIGS. 22A-22C, the extraction device extends from the first arm in a lateral direction opposite the distal ends of the jaws, e.g., laterally extending jaws. According to an aspect, the extraction device 312 comprises a T-handle 112' and a strike plate 140' (including an upper face 140a' and a lower face 140b') which are releasably connectable to the connector member 310 similar to the manner in which the T-handle and the strike plate are joined to the proximal end of the implant extractor 100, as described above.

Figure 23:
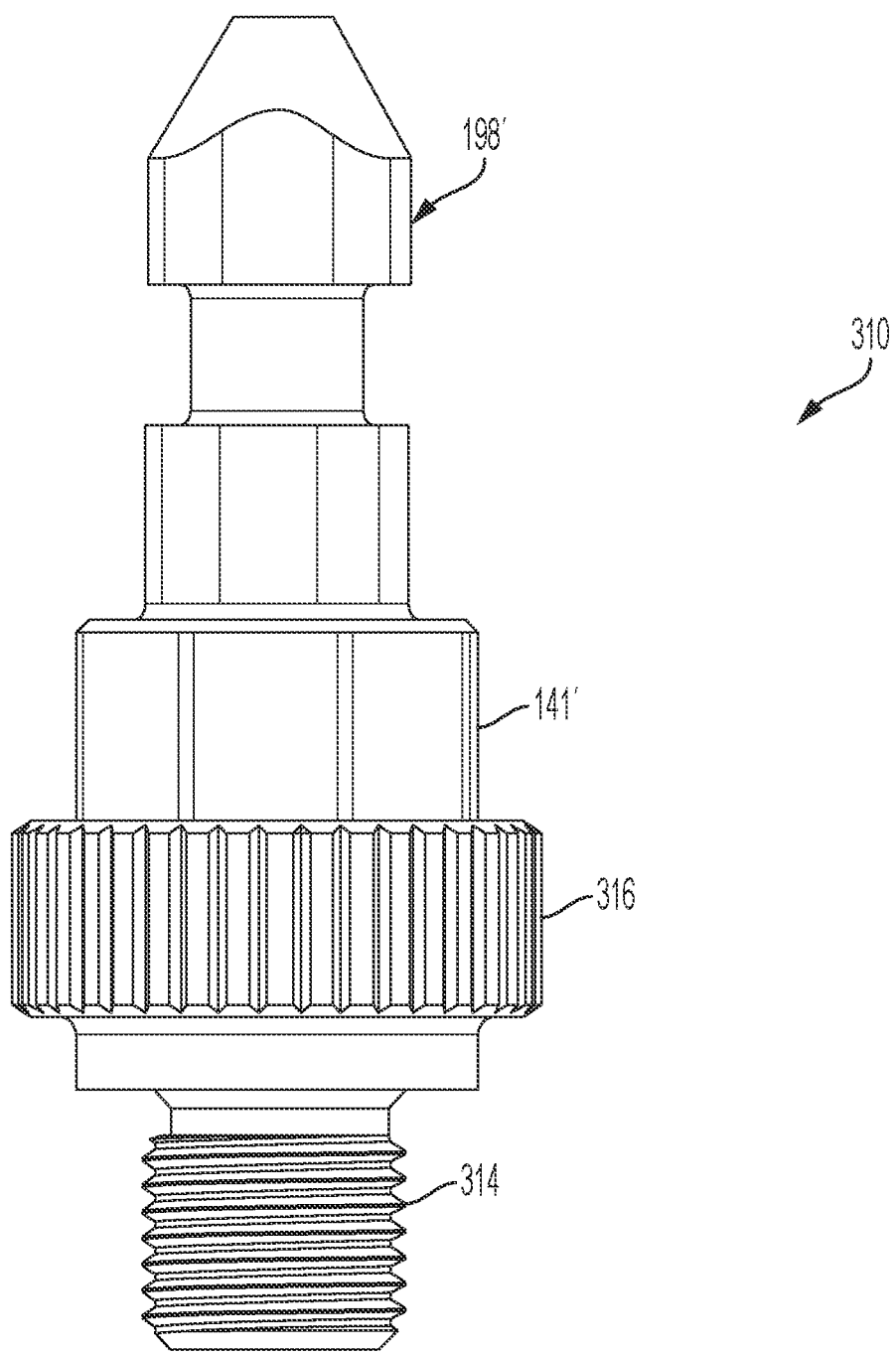
FIG. 23 is an elevation view of a connector configured for use in the implant extractor of FIGS. 22A-22C.

Referring to FIG. 23, the connector member 310 includes a fastener 314 in the form of external threading at a first end thereof for engaging the corresponding fastener in the form of internal threading 302 of the transverse opening 300. While illustrated as being cooperating threading, the fastener of the connector member and the transverse opening may assume other forms including, without limitation, a J-slot connection, press-fit, Luer lock, slip-fit with ball detent, and the like. Adjacent threading 314, the connector member further includes a radially projecting turning knob 316, the exterior of which is desirably provided with grip-enhancing structure such as knurling or, as illustrated, ribs to facilitate threading of the connector member into the transverse opening in the first arm. On the side of knob 316 opposite fastener structure 314 is a polygonal base 141' for receiving an unillustrated correspondingly shaped opening in the strike plate 140'. The connector member further includes a quick connect 198' that is structured to releasably engage with a corresponding quick connector, e.g., a biased locking member 199' (FIG. 22B) carried by the extraction device 312. The T-handle 112' holds the strike plate 140' in place and both are easily removable from the quick connect 198' upon depression of the biased locking member 199'.

When the extraction device 312 is secured to the implant extractor 100' and the implant extractor is clamped on an implant in the manner described above, a user may strike the lower face 140b' of the strike plate 140' with a hammer, mallet or the like, in order to dislodge the implant from bone.

Figure 24A:
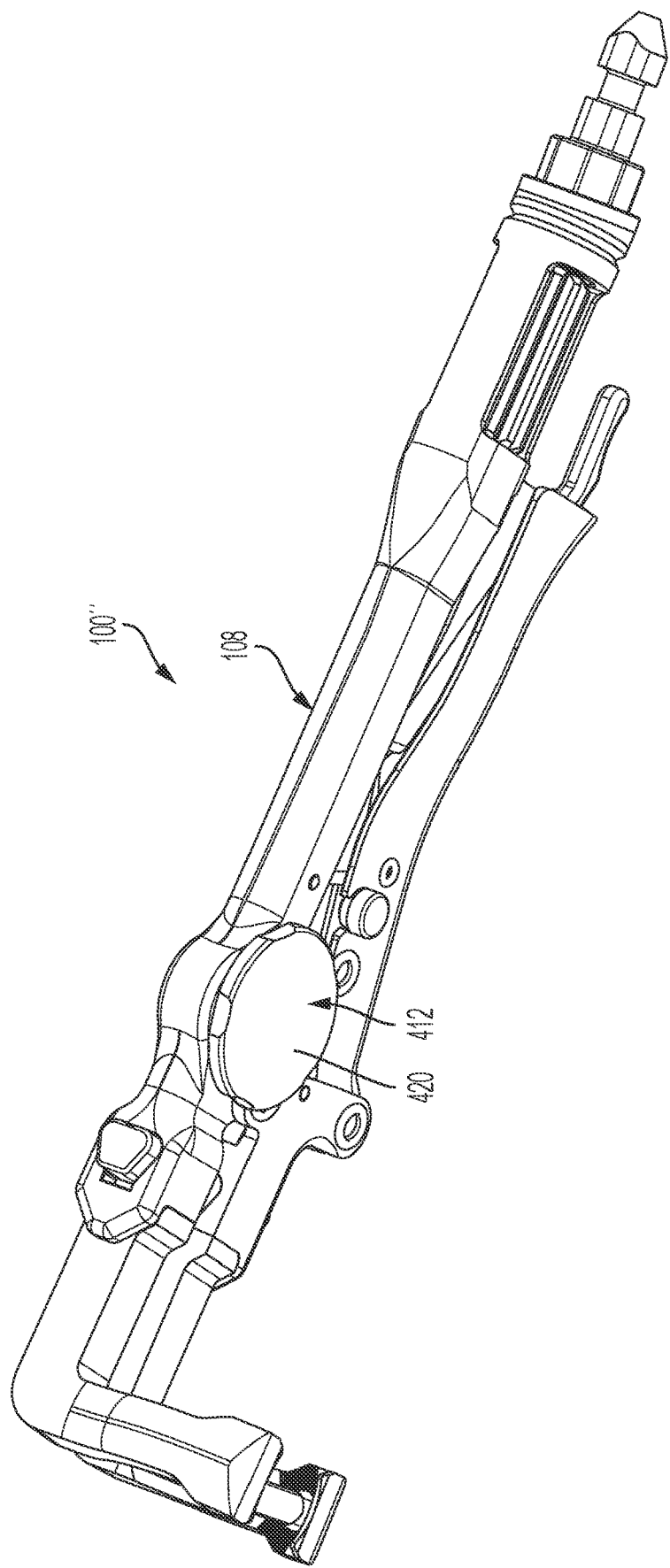
FIG. 24A is a perspective view of yet another exemplary embodiment of an implant extractor in accordance with the subject disclosure.
Figure 24B:
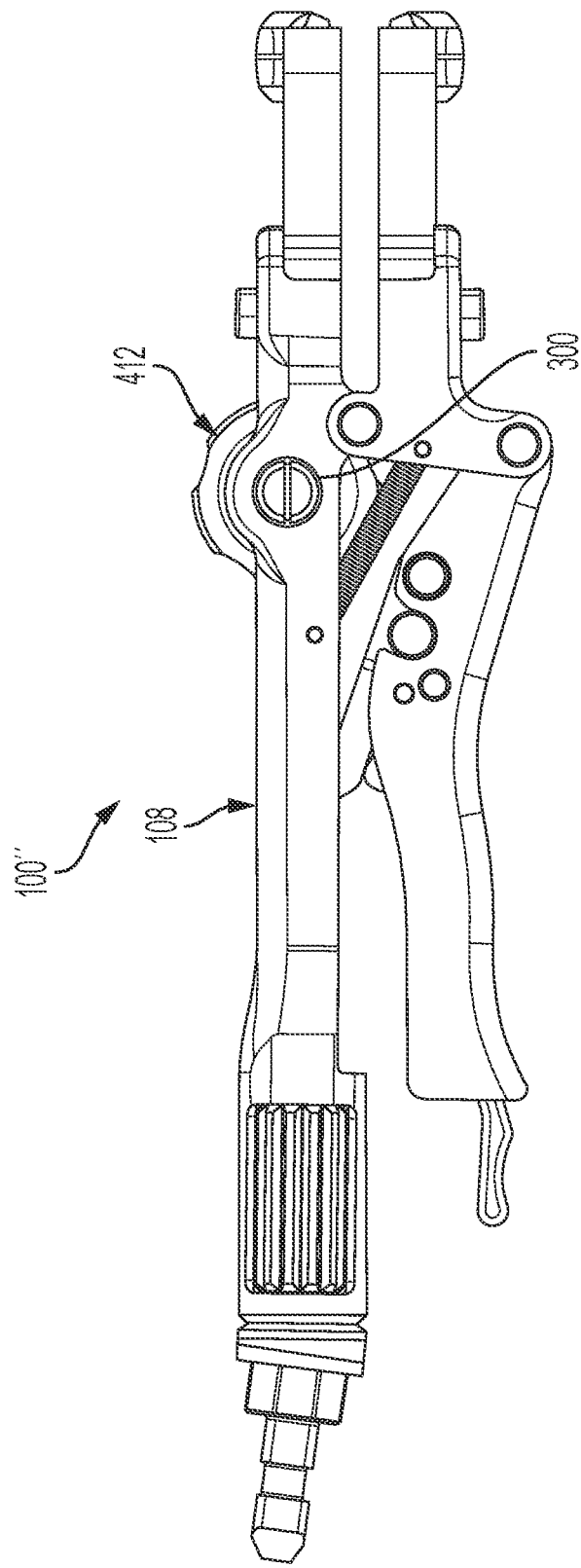
FIG. 24B is side view of the implant extractor of FIG. 24A.
Figure 25A:
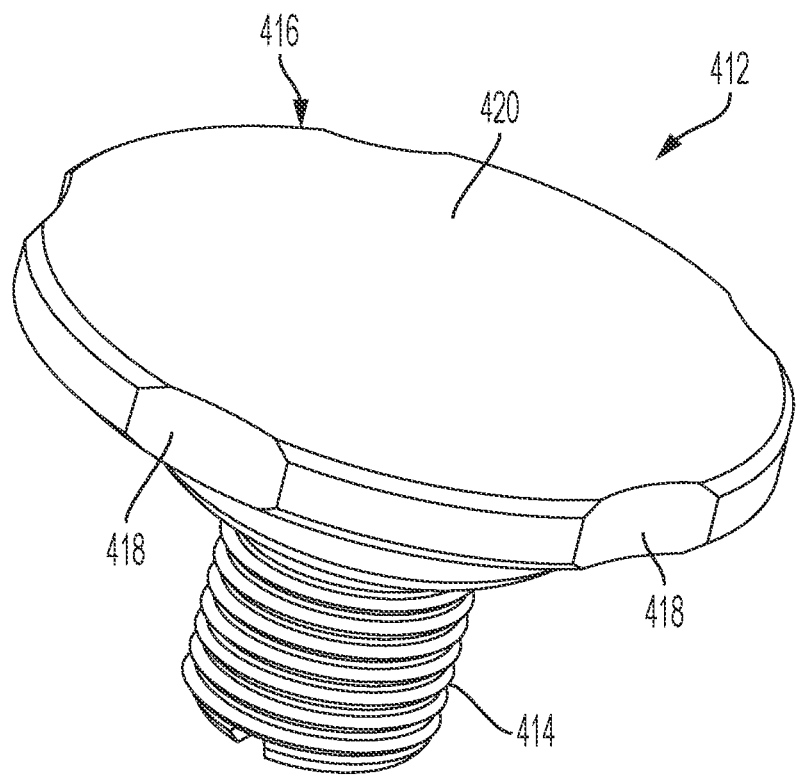
FIG. 25A is a top perspective view of an extraction device of the implant extractor of FIGS. 24A and 24B.
Figure 25B:
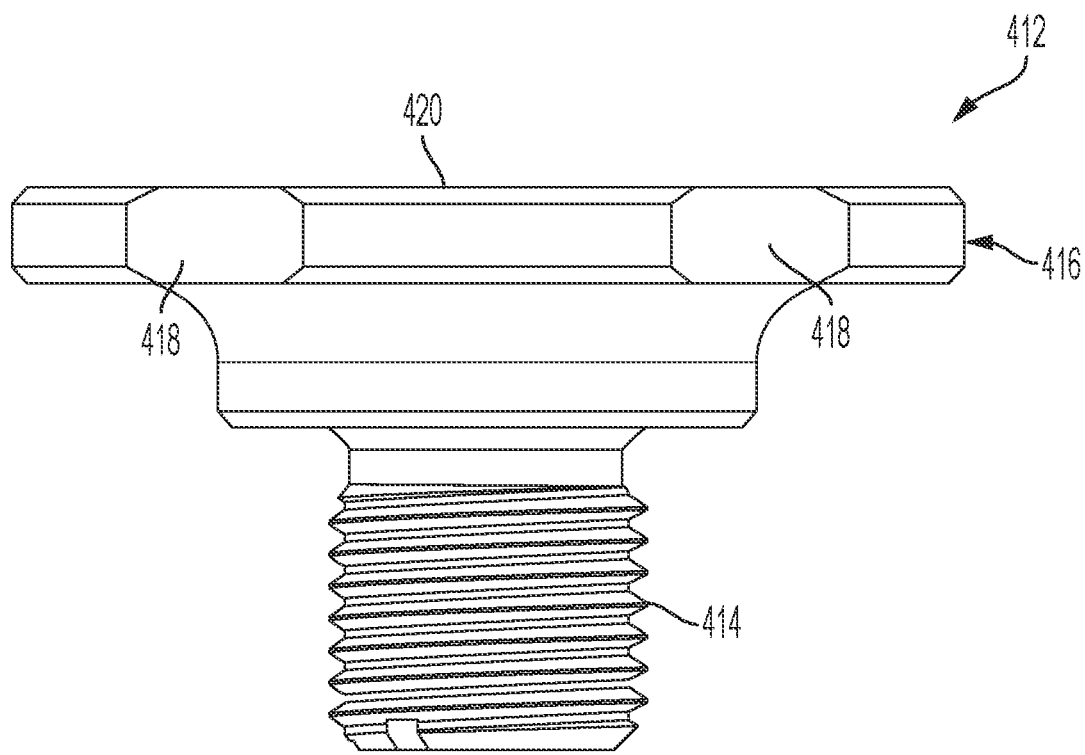
FIG. 25B is a side view of the extraction device of FIG. 25A.

Referring to FIGS. 24A and 24B, there is shown another exemplary embodiment of an implant extractor 100" according to the subject disclosure. Since the implant extractor 100" is structurally and functionally similar to implant extractor 100, only those aspects of the implant extractor 100" which materially depart in structure and/or function from the implant extractor 100 will be described in detail. In this regard, the implant extractor 100" includes an extraction device 412. In the illustrated example, the extraction device extends from the first arm in a lateral direction on the same side as the distal ends of the jaws, e.g., laterally extending jaws. As shown in FIGS. 25A and 25B, the extraction device includes a fastener 414 in the form of external threading for engaging the corresponding fastener in the form of internal threading 302 of the transverse opening 300 in the first arm 108. While illustrated as being cooperating threading, the fastener structures of the extraction device and the transverse opening may assume other forms including, without limitation, a J-slot connection, press-fit, Luer lock, slip-fit with ball detent, and the like. Adjacent threading 414, the extraction device further includes a radially projecting turning knob 416, the periphery of which is desirably provided with grip-enhancing structure such as a plurality of notches 418 for receiving a user's fingers to facilitate threading of the extraction device 412 into the transverse opening in the first arm. The exposed upper surface 420 defines a striking surface adapted for striking by a hammer, mallet or the like.

When the extraction device 412 is secured to the implant extractor 100" and the implant extractor is clamped on an implant in the manner described above, a user may strike the upper surface 420 of the extraction device with a hammer, mallet or the like, in order to dislodge the implant from bone.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. An implant extractor comprising:
   a second arm having a proximal end and a distal end;
   a first arm having:
      a proximal end,
      a distal end attached to a first jaw, and
      an adjustment mechanism about the distal end that includes:
         an adjuster having:
            a rotatable knob, and
            a rod housed completely within the first arm and extending into the rotatable knob and movable relative to the rotatable knob;
   a lever movable relative to the first arm, the lever having a proximal end engaged with the adjuster and a distal end pivotably connected to the second arm; and
   a link pivotably connected to the first and second arms, the link having a distal end attached to a second jaw.

2. The implant extractor of claim 1, further comprising a biasing member biasing the link and the first arm.

3. The implant extractor of claim 1, wherein the rod is a threaded rod threadedly engaged with the first arm.

4. The implant extractor of claim 1, wherein the rod includes at least one planar side.

5. The implant extractor of claim 4, wherein the rotatable knob has an opening with a planar side to cooperate with the planar side of the rod.

6. The implant extractor of claim 1, wherein the rod abuts a most proximal end of the lever.

7. The implant extractor of claim 1, wherein the first arm includes a cage having an opening for housing the rotatable knob.

8. The implant extractor of claim 1, wherein the first arm includes a quick connect about its proximal end.

9. The implant extractor of claim 1, further comprising a first jaw releasably attachable to the distal end of the first arm and a second jaw releasably attachable to the distal end of the link.

10. The implant extractor of claim 9, wherein the first and second jaws each include a slidable lock to slidingly engage a corresponding slidable lock on the first arm and link, respectively.

11. The implant extractor of claim 10, wherein the corresponding slidable lock on the first arm and link each includes a stop.

12. The implant extractor of claim 10, wherein the slidable lock is a dovetail.

13. The implant extractor of claim 10, wherein the slidable lock on each of the first and second jaws is a male dovetail and the corresponding slidable lock on each of the first arm and the link is a female dovetail.

14. The implant extractor of claim 10, further comprising a detent carried by one of the first jaw and the first arm or a detent carried by one of the second jaw and the link.

15. The implant extractor of claim 1, further comprising a locking cylinder on the lever movable between a locked position and an unlocked position, wherein in the locked position the locking cylinder maintains clamping engagement of the first and second jaws, and in the unlocked position the locking cylinder permits release of the first and second jaws from clamping engagement with an implant to be extracted.

16. The implant extractor of claim 10, further comprising a release lever on the second arm to release the first and second jaws from clamping engagement with an implant to be extracted.

17. The implant extractor of claim 1, wherein the first arm includes a transverse opening having fastener structure configured to releasably retain an extraction device.

18. An implant extractor comprising:
   a second arm having a proximal end and a distal end;
   a first arm having:
      a proximal end for attachment to an extraction device,
      a distal end for attachment to a first jaw, and
      an adjustment mechanism that includes:
         an adjuster having:
            a rotatable knob, and
            a rod entirely within the first arm and extending into the rotatable knob and movable relative to the rotatable knob, and
         a cage having an opening for housing the rotatable knob;
   a lever movable relative to first arm, the lever having a proximal end engaged with the adjuster and a distal end pivotably connected to the second arm; and
   a link pivotably connected to the first and second arms, the link having a distal end for attachment to a second jaw.

19. An implant extractor comprising:
   a second arm having a proximal end and a distal end;
   a first arm having:
      a proximal end for attachment to an extraction device,
      a distal end for attachment to a first jaw, and
      an adjustment mechanism that includes:
         an adjuster having:
            a rotatable knob, and
            a rod entirely within the first arm and extending into the rotatable knob and movable relative to the rotatable knob;
   a lever movable relative to first arm, the lever having a proximal end engaged with the adjuster and a distal end pivotably connected to the second arm;
   a locking cylinder on the lever movable between a locked position and an unlocked position, the locking cylinder including a first cylindrical portion and a second cylindrical portion smaller than the first cylindrical portion; and
   a link pivotably connected to the first and second arms, the link having a distal end for attachment to a second jaw.

* * * * *